(12) United States Patent
Kim

(10) Patent No.: US 12,258,545 B2
(45) Date of Patent: Mar. 25, 2025

(54) SUSTAINABLE CURTAIN WALL

(71) Applicant: The University Of North Carolina At Charlotte, Charlotte, NC (US)

(72) Inventor: Kyoung Hee Kim, Charlotte, NC (US)

(73) Assignee: The University Of North Carolina At Charlotte, Charlotte, NC (US)

( * ) Notice: Subject to any disclaimer, the term of this patent is extended or adjusted under 35 U.S.C. 154(b) by 886 days.

(21) Appl. No.: 17/070,124

(22) Filed: Oct. 14, 2020

(65) Prior Publication Data

US 2021/0108166 A1  Apr. 15, 2021

Related U.S. Application Data

(60) Provisional application No. 62/972,841, filed on Feb. 11, 2020, provisional application No. 62/915,077, filed on Oct. 15, 2019, provisional application No. 62/915,088, filed on Oct. 15, 2019.

(51) Int. Cl.
*C12M 1/00* (2006.01)
*E04B 2/96* (2006.01)
*E06B 3/66* (2006.01)
*E06B 7/28* (2006.01)

(52) U.S. Cl.
CPC ............... *C12M 21/02* (2013.01); *E04B 2/96* (2013.01); *E06B 3/6612* (2013.01); *E06B 7/28* (2013.01)

(58) Field of Classification Search
CPC ...... C12M 21/02; C12M 23/48; C12M 41/48; C12M 23/50; C12M 41/06; C12M 41/12; C12M 41/30; E04B 2/96; E04B 2/88; E06B 3/6612; E06B 7/28; E06B 7/14;
(Continued)

(56) References Cited

U.S. PATENT DOCUMENTS 4,662,135 A * 5/1987 Tanikawa .................. E04B 2/90
                                                  52/489.1
5,765,881 A * 6/1998 Perner .................... F16L 23/032
                                                  285/415
(Continued)

FOREIGN PATENT DOCUMENTS

| CA | 2336524 A1 | * | 11/2000 | |
| CH | 663813 A | * | 1/1988 | ............... E04B 2/94 |
| CN | 110591890 A | | 12/2019 | |

(Continued)

OTHER PUBLICATIONS

Machine Translation of Legendre at al. (WO2013011240), 2013 (Year: 2013).*

(Continued)

*Primary Examiner* — Lydia Edwards
(74) *Attorney, Agent, or Firm* — Clements Bernard Walker; Christopher L. Bernard; Devin Cummins

(57) ABSTRACT

A microalgae curtain wall includes photobioreactors, an interior glass panel, an exterior glass panel, and transoms. The photobioreactors are adapted to receive sunlight and carbon dioxide to grow microalgae received therein. The exterior glass panel is offset from the interior glass panel forming a gap therebetween. The transoms hold the interior glass panel and the exterior glass panel therebetween. The transoms suspend the photobioreactors in the gap and between the interior glass panel and the exterior glass panel.

17 Claims, 17 Drawing Sheets

(58) Field of Classification Search
CPC .. E06B 2007/145; E06B 1/366; E06B 3/5427; E06B 7/02; E06B 9/24; H02S 20/26
See application file for complete search history.

(56) References Cited

U.S. PATENT DOCUMENTS

| | | | | |
|---|---|---|---|---|
| 2008/0254529 | A1* | 10/2008 | Freeman | C12M 31/10 435/243 |
| 2019/0316067 | A1 | 10/2019 | Melchiorri | |

FOREIGN PATENT DOCUMENTS

| | | | | |
|---|---|---|---|---|
| KR | 101065044 | B1* | 9/2011 | |
| WO | 2013011240 | A2 | 1/2013 | |
| WO | WO-2017118342 | A1* | 7/2017 | E04B 1/76 |

OTHER PUBLICATIONS

Feb. 3, 2022 International Search Report issued in corresponding International Application No. PCT/US21/54912.

United Nation, "World Urbanization Prospects," Last modified in 2014. https://esa.un.org/unpd/wup/publications/files/wup2014-highlights.pdf, website.

U.S. Department of Energy, "National Algal Biofuels Technology Review," Last modified in Jun. 2016. https://www.energy.gov/sites/prod/files/2016/06/f33/national_algal_biofuels_technology_review.pdf,website.

World Health Organization, "Ambient air pollution: A global assessment of exposure and burden of disease," Last modified in 2016, http://apps.who.int/iris/bitstream/handle/10665/250141/9789241511353-eng.pdf;jsessionid=C2B6C0A2F98E71C670D2D24917F04AD6?sequence=1.

U.S. Energy Information Administration, "Annual EnergyOutlook 2015,". Last modified in Apr. 2015. https://www.eia.gov/outlooks/aeo/pdf/0383(2015).pdf, website.

Ghada Mohammad Elrayies, "Microalgae: Prospects for greenerfuture buildings", Journal of Renewable and Sustainable Energy Reviews. vol 81, pp. 1175-1191, Jan. 2018.

A. Giostri, M.Binotti, and E. Macchi, "Microalgae cofiring in coal power plants: innovative system layout and energy analysis", Journal of Renewable Energy, vol. 95, pp. 449-464, Sep. 2016.

Kim K, "A Feasibility Study of an Algae Facade System",Proceeding of International Conference in Sustainable Buildings, Seoul, South Korea, pp. 333-341, Jun. 2013.

"Carbon T.A.P.", accessed from, http://porturbanism.com/work/carbon-t-a-p/;website, 2009.

"Urban Algae Canopy", Last modified in 2014. http://www.carloratti.com/wp-contenuploads/2014/05/20140430_Domus.pdf,website.

The Algae Dome: A food-producing pavilion. Access from https://space10.io/algae-dome/;wesbite, 2017.

"Smart Material Houses: BIQ". Access from https://www.ba-hamburg.de/en/projects/the-building-exhibition-withinthe-building-exhibition/smart-material-houses/biq/projekt/biq.html, 2013.

"Algae Curtain". Access from http://loop.ph/portfolio/algae-curtain/; website, 2012.

\* cited by examiner

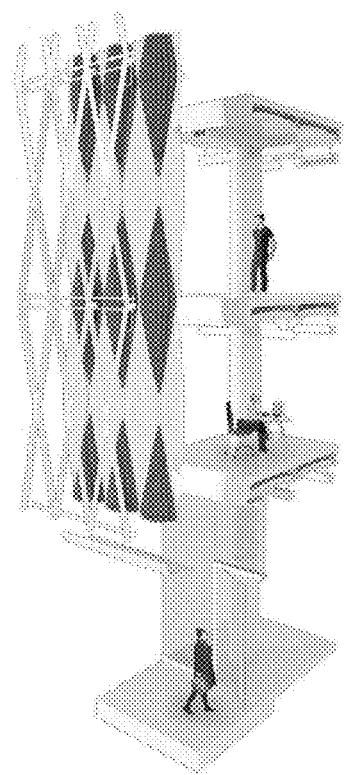
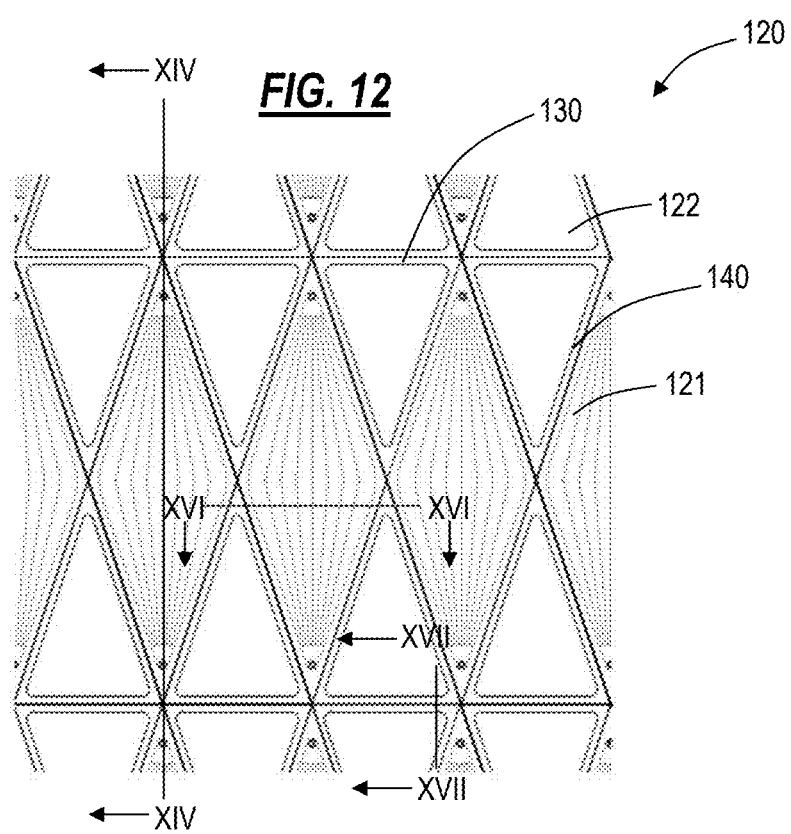
FIG. 12
FIG. 13

SUSTAINABLE CURTAIN WALL

PRIORITY CLAIM

This application claims the benefit of U.S. Provisional Patent Application Ser. No. 62/915,088 entitled "MICROALGAE BUILDING ENCLOSURE SYSTEM; BIOCATALYST BUILDING ENCLOSURE SYSTEM; DIVIDED, INFLATED, STRANDED, SUSPENDED, AND WOVEN MICROALGAE BUILDING ENCLOSURE SYSTEMS," filed on Oct. 15, 2019, U.S. Provisional Patent Application Ser. No. 62/915,077 entitled "MICRO-OCULI BUILDING ENCLOSURE SYSTEM: KINETIC AND STATIC APPLICATION," filed on Oct. 15, 2019, and U.S. Provisional Patent Application Ser. No. 62/972,841 entitled "BIOCATALYST BUILDING ENCLOSURE SYSTEM," filed on Feb. 11, 2020, which are hereby incorporated by reference.

TECHNICAL FIELD

The present disclosure generally relates to micro algae systems. More particularly, the present disclosure relates to systems and methods for micro algae systems with an integrated microalgae curtain wall for building enclosure.

BACKGROUND

Over the past few decades, microalgae have been cultivated for various uses in agricultural, aquacultural, pharmaceutical, and food industries due to its fast growth rate and a wide array of biodiversity growing in a wide range of habitats. Microalgae offers ecological sustainability by improving soil quality, water quality, and air quality while encouraging biodiversity and minimizing greenhouse gas emissions. Furthermore, it serves socioeconomic sustainability by offering social well-being (e.g. employment, food security), energy security, and resource conservation. Algae's photosynthesis with its fast growth rate includes a number of benefits. These benefits include the production of $O_2$ and sequestration of $CO_2$, which can be used to offset human driven $CO_2$ emission. Further, microalgae can be used, among other things, to generate biofuel, which can reduce our dependence on non-renewable resources. Use of microalgae to produce $O_2$ and to generate biofuel can offer ecological and economic benefits.

Tall building enclosures, such as office buildings and apartments, represent a significant amount of the electricity use, energy use and greenhouse gas emissions, particularly those in dense urban areas. Glass enclosures have been preferred in contemporary buildings by architects and owners due to design opportunities such as daylighting, view-out and aesthetics. Aesthetic appeal of transparency and lightness of glass is unique attributes that other building materials do not offer. Further, innovation in glass technology over the past decades has pushed the boundary of design opportunities and technical advancement for glass enclosures.

In addition to energy attributes, constructability of building enclosure systems is important in that the high-rise buildings and the dense urban site have additional construction challenges such as access to the site, building material storage and space for installation equipment.

Recently, building-integrated microalgae facades have drawn the attention of architects and designers in the field of net zero architecture due to its effective role in enhancing building energy efficiency, producing on-site biofuel as well as reducing air pollutions and processing wastewater treatment. It is estimated that such tall building enclosures fitted or retrofitted with microalgae facades could significantly reduce energy consumption as compared to the original building or a building constructed without microalgae facades.

In view of the above, there is a need for a cost effective lightweight prefabricated microalgae facade for use within a microalgae system, that integrates with tall building enclosures, with longevity and quality control that comply with building codes and national industry standards.

The above-described background relating to microalgae facades is merely intended to provide a contextual overview of some current issues and is not intended to be exhaustive. Other contextual information may become apparent to those of ordinary skill in the art upon review of the following description of exemplary embodiments.

SUMMARY

The present disclosure generally provides a microalgae system including a microalgae curtainwall for a building that serves as a building enclosure that provides solar heat control, daylight transmission, thermal insulation, and structural integrity to the building, replacing building enclosures, such as low energy efficient windows.

In one exemplary embodiment, the present disclosure provides a microalgae curtain wall. The microalgae curtain wall includes photobioreactors, an interior glass panel, an exterior glass panel, transoms, and mullions. The photobioreactors are adapted to receive sunlight and carbon dioxide to grow microalgae received therein. The exterior glass panel is offset from the interior glass panel forming a gap therebetween. The transoms hold the interior glass panel and the exterior glass panel therebetween. The transoms suspend the photobioreactors in the gap and between the interior glass panel and the exterior glass panel.

In one embodiment of the microalgae curtain wall, the photobioreactors are arranged in an array forming open areas therebetween that are adapted to allow a view therethrough.

In another embodiment of the microalgae curtain wall, the transoms include at least one upper photobioreactor support bracket and at least one lower photobioreactor support bracket with vertically slotted holes that hold and suspend the photobioreactors therebetween.

In a further embodiment of the microalgae curtain wall, the microalgae curtain wall further includes mullions holding the interior glass panel and the exterior glass panel therebetween and positioned at sides of the photobioreactors. Optionally, the mullions are offset from the sides of the photobioreactors with a localized bracket. Optionally, each of the transoms and the mullions include glass support brackets for the interior glass panel and the exterior glass panel, forming a seal therewith, and wherein the transoms, the mullions, the interior glass panel, and the exterior glass panel form an insulated glass structure. And optionally, the microalgae curtain wall, including the transoms, the mullions, the interior glass panel, the exterior glass panel, and the photobioreactors, forms a modular, prefabricated component.

In yet another embodiment of the microalgae curtain wall, the photobioreactors include multiple photobioreactor components joined together by one or more brackets with a gasket therebetween. Optionally, each of the photobioreactor components includes a key on opposing sides with the one or more brackets received therein.

In yet a further embodiment of the microalgae curtain wall, the photobioreactors are arranged in an array with at least one of a partially overlapping and interlocking pattern.

In another exemplary embodiment, the present disclosure provides a microalgae system. The microalgae system includes a microalgae storage tank and a microalgae curtain wall. The microalgae storage tank adapted to store microalgae cultures. The microalgae curtain wall includes photobioreactors, an interior glass panel, an exterior glass panel, and transoms. The photobioreactors are adapted to receive the microalgae cultures from the microalgae storage tank and to grow microalgae. The exterior glass panel is offset from the interior glass panel forming a gap therebetween. The transoms hold the interior glass panel and the exterior glass panel therebetween and suspend the photobioreactors in the gap and between the interior glass panel and the exterior glass panel.

In one embodiment of the microalgae system, the photobioreactors are arranged in an array forming open areas therebetween that are adapted to allow a view therethrough.

In another embodiment of the microalgae system, the transoms include at least one upper photobioreactor support bracket and at least one lower photobioreactor support bracket with vertically slotted holes that hold and suspend the photobioreactors therebetween.

In a further embodiment of the microalgae system, the photobioreactors include multiple photobioreactor components joined together by one or more brackets with a gasket therebetween.

In yet another embodiment of the microalgae system, the microalgae system further includes an oxygen outlet line adapted to supply oxygen produced by the microalgae to a heating, ventilation, and air conditioning system of the building.

In yet a further embodiment of the microalgae system, the microalgae system further includes onsite energy production adapted to receive the microalgae from the microalgae curtain wall and convert the microalgae into energy.

In still another embodiment of the microalgae system, the microalgae system further includes a dewatering plant adapted to separate the microalgae from the microalgae curtain wall from water therein.

In another embodiment of the microalgae system, the curtain wall further includes mullions holding the interior glass panel and the exterior glass panel therebetween and positioned at sides of the photobioreactors. At least one of the mullions and the transoms are anchored to a building structure. Optionally, the microalgae curtain wall, including the transoms, the mullions, the interior glass panel, the exterior glass panel, and the photobioreactors, forms a modular component, and wherein the microalgae system includes a plurality of the modular component. And optionally, each of the transoms and the mullions include glass support brackets for the interior glass panel and the exterior glass panel, forming a seal therewith, and wherein the transoms, the mullions, the interior glass panel, and the exterior glass panel form an insulated glass structure.

BRIEF DESCRIPTION OF THE DRAWINGS

The present disclosure is illustrated and described herein with reference to the various drawings, in which like reference numbers are used to denote like system components/method steps, as appropriate, and in which:

FIG. 12 is a partially exploded schematic illustration of an embodiment of the microalgae curtain wall of FIG. 1;

FIG. 13 is a schematic illustration of a partial elevation of the microalgae curtain wall of FIG. 12;

DESCRIPTION OF EXEMPLARY EMBODIMENTS

In various embodiments, the present disclosure relates to systems and methods for a microalgae system. In particular, the microalgae system includes a microalgae curtain wall that serves as a primary building enclosure, such as a traditional window, that provides holistic utilitarian functions of adequate thermal and structural performance, good daylight transmission, shading efficacy as well as air tightness and water tightness in accordance with industry standards.

The microalgae curtain wall, through microalgae growth therein, improves indoor and outdoor air quality through $O_2$ production and $CO_2$ bio fixation as a result of photosynthesis by the microalgae. As another benefit, the microalgae harvested from the microalgae curtain wall can be extracted and converted into renewable fuel stocks, such as biomass or biofuel. The renewable fuel converted from the microalgae can offset building energy consumption from the built environment and can be integrated into the green fuel industry.

For example, the microalgae curtain wall can produce the heat as a byproduct to supply the heat demands of the building, such as for space heating and for domestic hot water. Furthermore, the microalgae curtain wall can serve as a cost-effective and sustainable infrastructure for domestic wastewater treatment due to the ability of microalgae to provide oxygenation by photosynthesis and water sanitation.

As will be discussed in greater detail below, in some embodiments, the microalgae curtain wall is prefabricated, which can further contribute to lower development and construction costs, resulting in a cost effective and durable curtain wall that can be retrofitted to existing buildings and incorporated into new construction.

In various embodiments, the present disclosure further relates to systems and methods for a micro-oculi building enclosure system. The micro-oculus building enclosure system 300 includes micro-oculus shaders that are adapted to control daylight transmission and shading therethrough while producing energy via photovoltaic elements. In dynamic configurations, the micro-oculus shaders are rotatable allowing for dynamic control over the daylight transmission and solar heat gain as well as for optimizing the energy production thereof.

In various embodiments, the present disclosure further relates to systems and methods for a photocatalytic enclosure system. The photocatalytic enclosure system includes an array of open cells that are coated with Titanium Dioxide that acts as a catalyst for removing air pollution. In embodiments, the photocatalytic enclosure system encapsulates the array of open cells between a double skin facade that is adapted to purify air flowing therethrough.

Figure 1:
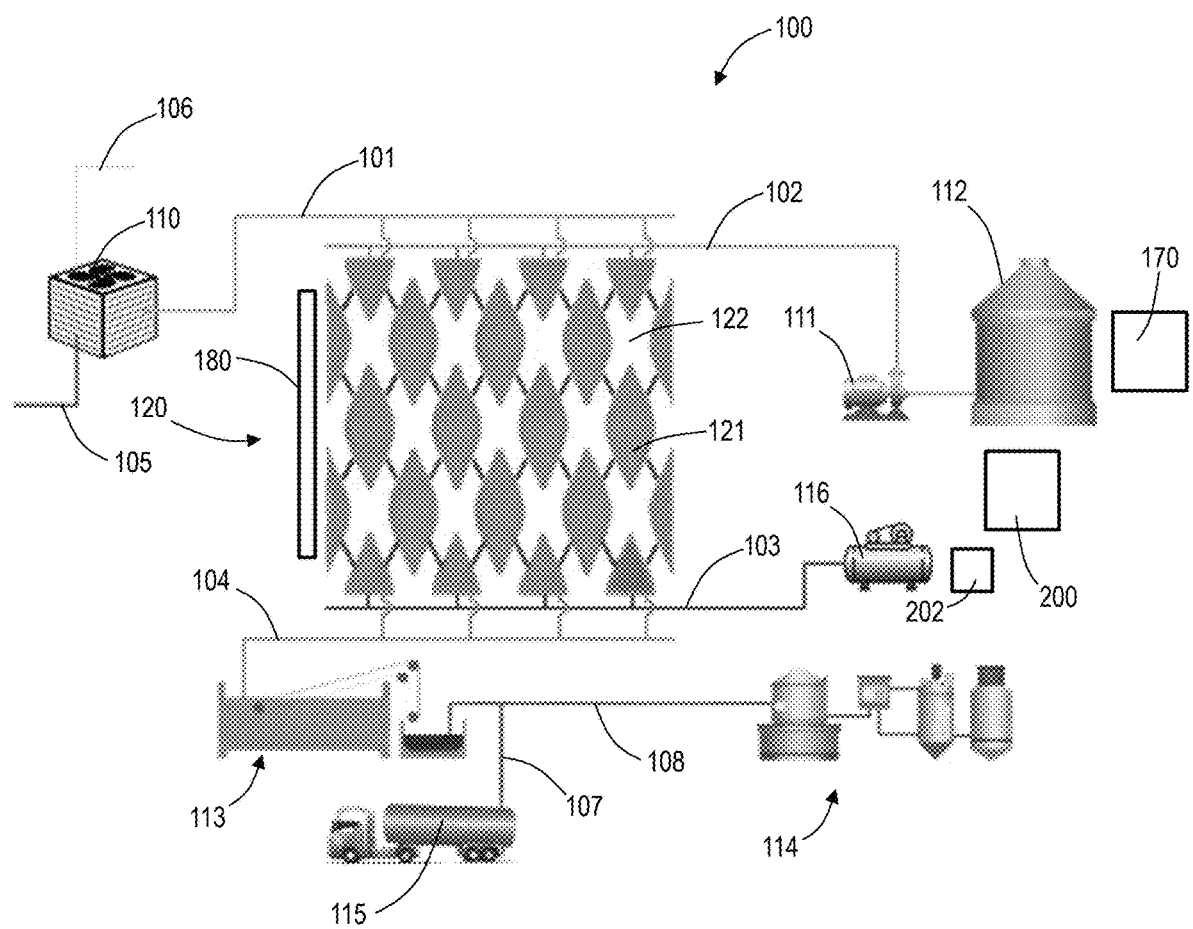
FIG. 1 is a schematic illustration of a microalgae system.

FIG. 1 is a schematic illustration of a microalgae system 100. The microalgae system 100 includes a microalgae curtain wall 120, a microalgae storage tank 112, and a dewatering facility 113. The microalgae curtain wall 120 is a facade for a building that serves as a building enclosure. In embodiments, the microalgae curtain wall is adapted to replace glass panels enclosures for buildings. The microalgae curtain wall 120 includes at least one photobioreactor 121 area and at least one vision area 122. In the embodiments illustrated, the microalgae curtain wall 120 includes an array of photobioreactors 121 with vision areas 122 interspersed within the array of photobioreactors 121. The photobioreactors 121 are adapted to encourage microalgae growth by providing a nutrient-rich environment. Further, the growth density of the microalgae provides shading to the interior space. The photobioreactors 121 include a cavity adapted to receive microalgae cultures and are formed of a material that permits sunlight to pass therethrough to the microalgae. The vision areas 122 are adapted to allow view-out by building occupants and daylighting penetration into the building.

The microalgae storage tank 112 is adapted to store microalgae for distribution to the photobioreactors 121. In particular, the microalgae storage tank 112 is adapted to store young microalgae cultures. In some embodiments, the microalgae storage tank 112 is also adapted to store nutrients, water, and the like that are used to facilitate microalgae growth. The nutrients, water, and the like can be stored in separate containers from the young microalgae cultures within the microalgae storage tank 112 or in a separate microalgae storage tank 112 altogether.

The microalgae is provided from the microalgae storage tank 112 to the photobioreactors 121, such as by a pump 111 and a microalgae inlet line 102. In embodiments, the microalgae inlet line 102 supplies the microalgae to a top of the microalgae curtain wall 120, such as at a top of each of the photobioreactors 121. Water, nutrients, and the like, are also provided to the photobioreactors 121, such as by the microalgae inlet line 102.

Air containing $CO_2$ is supplied to the photobioreactors 121, such as by a compressor 116 and an air inlet line 103. In embodiments, the air inlet line 103 supplies the $CO_2$ containing air to a bottom of the microalgae curtain wall 120, such as at a bottom of each of the photobioreactors 121. In some embodiments, the compressor 116 integrates a Ultraviolet-C (UVC) light tunnel to disinfect harmful bacteria and viruses in the $CO_2$ containing air.

The $O_2$ produced by the microalgae is removed from the photobioreactors 121 using an air outlet line 101. The air outlet line directs the O2 produced by the microalgae away from the photobioreactors 121 for release into the atmosphere or for a specific use, such as for direct injection of the $O_2$ into the Heating, Ventilation, and Air Conditioning system (HVAC) 110 of the building. Moisture from the air can be extracted via a moisture extraction line 105, while the $O_2$ rich air can be supplied to the building via an oxygen release line 106.

The microalgae is extracted from the photobioreactors 121 via a microalgae outlet line 104 and supplied to the dewatering facility 113. In embodiments, the microalgae is gravity fed from the photobioreactors 121 to the dewatering facility 113. However other methods, such as using pumps, is also contemplated. The dewatering facility 113 is adapted to separate the microalgae from water. In embodiments, the water is directed for other uses, and in other embodiments, the water is recycled back to the microalgae storage tank 112 for reuse in the photobioreactors 121 or supply heat for the space heating and water heating demand.

The dewatering facility 113 can include a sump or storage tank that holds the microalgae until the microalgae is needed for further distribution. In embodiments, the microalgae system 100 further includes at least one of an onsite energy production system 114 and microalgae transport 115. Onsite and offset outlet lines 107, 108 direct the microalgae for further use. The onsite energy production system 114 is adapted to use the microalgae as fuel and is adapted to provide energy for use. The microalgae transport 115 is adapted to transport the microalgae to processing plants for further use of the microalgae.

In embodiments, the various lines of the microalgae system including the air outlet line 101, the microalgae inlet line 102, the air inlet line 103, the microalgae outlet line 104, the offsite outlet line 107, and the onsite outlet line 108 are pipes formed of a material that will not react with microalgae, such as Polyvinyl Chloride (PVC) pipes.

In embodiments, the microalgae system 100 includes a controller 200, a heat exchanger 170, and light panel 180, such as a panel of Light Emitting Diode (LEDs). The controller 200 is configured to monitor the microalgae system 100, such as by the use of sensors positioned at varying positions within the system, and to control the various flows and temperature throughout the system. In some embodiments, the heat exchanger 170 conditions algae medium to regulate the temperature of the photobioreactors 121 to maintain the microalgae with optimal temperature ranges for growth thereof. In embodiments, the heat exchanger 170 is integrated with the storage tank 112 to regulate extreme cold and hot temperatures in the photobioreactors 121. In embodiments, the light panel 180 includes optical fibers. The light panel 180 is adapted to at least provide an artificial light source at night, to stimulate growth of the microalgae. In some embodiments, the light panel 180 is adapted to emit light that kills harmful organisms, such as bacteria, to protect the microalgae.

Figure 2:
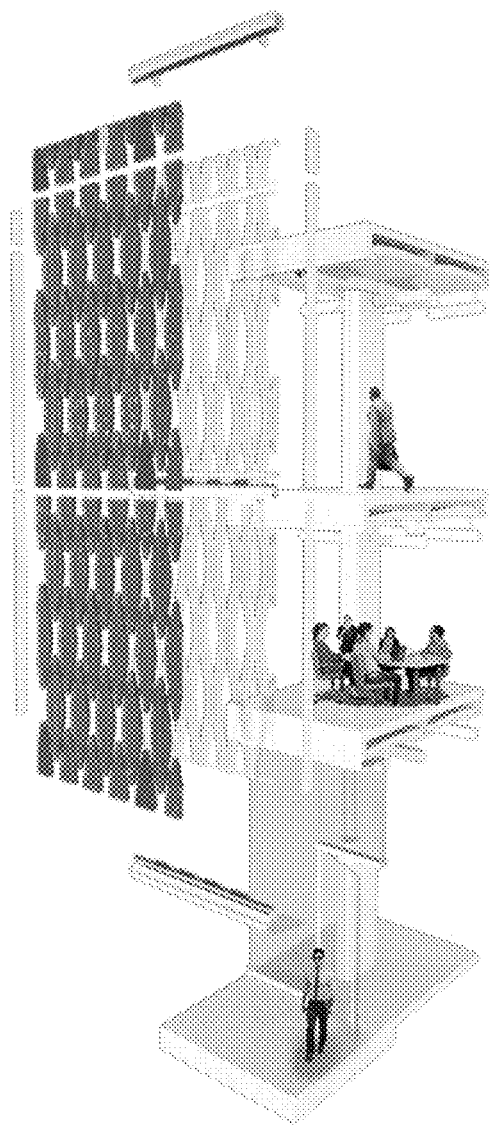
FIG. 2 is a partially exploded schematic illustration of an embodiment of the microalgae curtain wall of FIG. 1.
Figure 3:
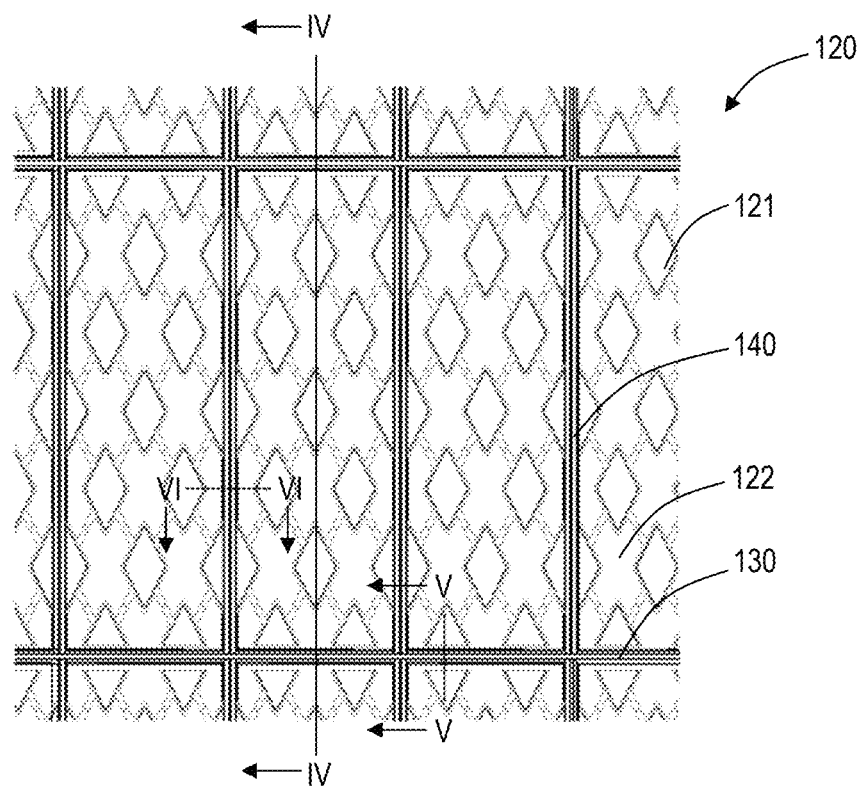
FIG. 3 is a schematic illustration of an elevation of the microalgae curtain wall of FIGS. 1-2.
Figure 4:
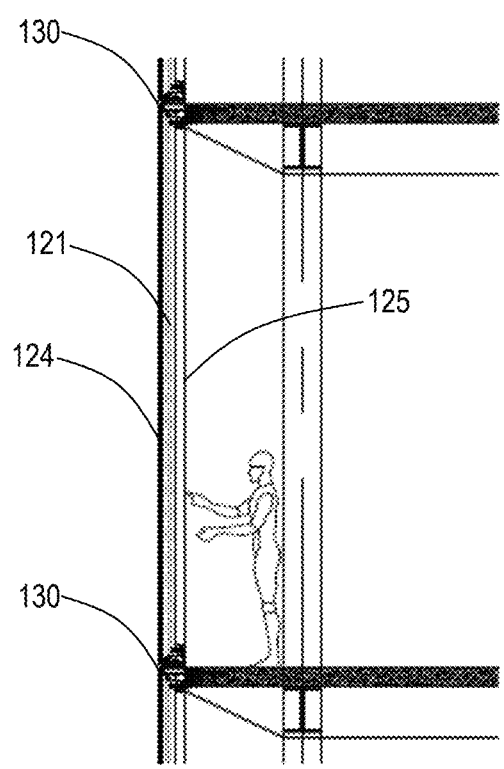
FIG. 4 is a schematic illustration of a cross-section of the microalgae curtain wall of FIG. 3 taken along the line IV-IV.
Figure 5:
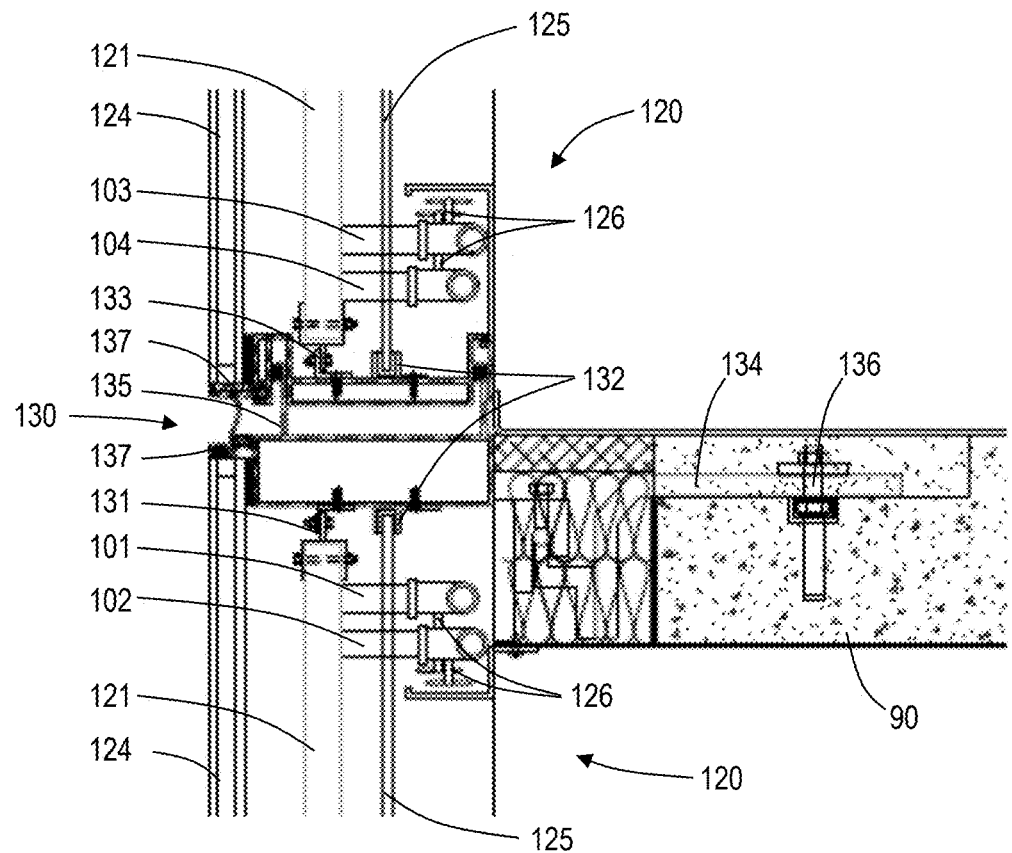
FIG. 5 is a schematic illustration of a partial cross-section of the microalgae curtain wall of FIG. 3 taken along the line V-V.
Figure 6:
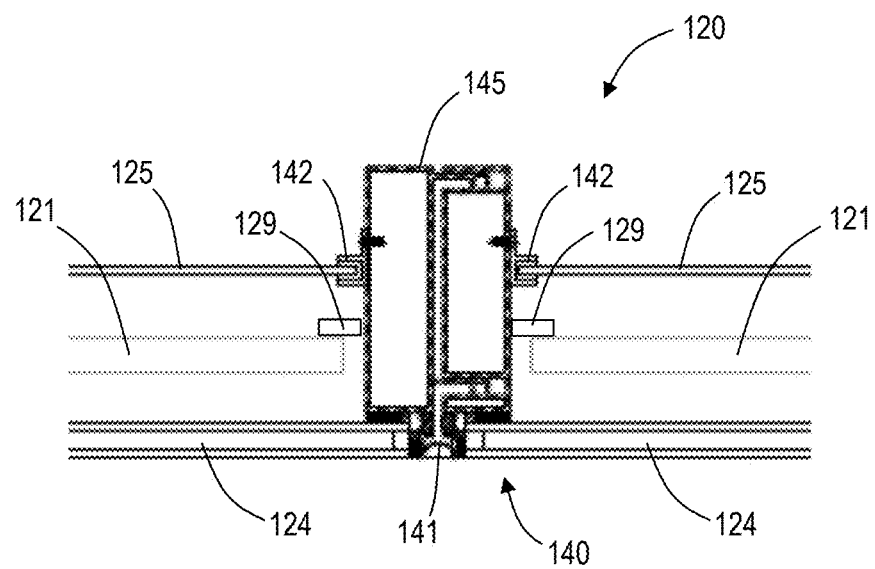
FIG. 6 is a schematic illustration of a partial cross-section of the microalgae curtain wall of FIG. 3 taken along the line VI-VI.

FIG. 2 is a partially exploded schematic illustration of an embodiment of the microalgae curtain wall of FIG. 1. FIG. 3 is a schematic illustration of an elevation of the microalgae curtain wall of FIGS. 1-2. FIG. 4 is a schematic illustration of a cross-section of the microalgae curtain wall of FIG. 3 taken along the line IV-IV. FIG. 5 is a schematic illustration of a partial cross-section of the microalgae curtain wall of FIG. 3 taken along the line V-V. FIG. 6 is a schematic illustration of a partial cross-section of the microalgae curtain wall of FIG. 3 taken along the line VI-VI.

In the embodiment illustrated in FIGS. 2-6, The photobioreactors 121 are suspended by transoms 130 between mullions 140 and between glass panels 124, 125.

In embodiments, and as shown in FIGS. 3-6, an exterior glass panel 124 is offset from an interior glass panel 125 forming an air cavity 128 therebetween within which the photobioreactors 121 are suspended. In embodiments, the interior glass panel 125 is a single pane of glass, while the exterior glass panel 124 is insulated panel, such as a dual pane glass panel with an air gap for insulation therein. However, other types and styles of glass panels for each of the interior glass panel 125 and the exterior glass panel 124 are also contemplated.

referring to FIG. 5, the transom 130 includes interior glass support brackets 132 and exterior glass support brackets 137 mounted to a body 135 thereof In embodiments, the body 135 is a single body, and in other embodiments, the body 135 is formed of two separate bodies joined together. The interior and exterior glass support brackets 132, 137 are adapted to support the interior and exterior glass panels 125, 124. In embodiments, the interior and exterior glass support brackets 132, 135 are adapted to form a seal with the interior and exterior glass panels 125, 124. In some embodiments, a single transom 130 is adapted to support the top of a first set of the interior and exterior glass panels 125, 124 and the bottom of a second set of the interior and exterior glass panels 125, 124. In another embodiment, separate transoms 130 are used.

In the embodiment illustrated, the transom 130 includes an upper photobioreactor support bracket 131 and a lower photobioreactor support bracket 133. While a single transom 131 is shown with both the upper photobioreactor support bracket 131 and the lower photobioreactor support bracket 133, in other embodiments, separate transoms 130 are used. The upper photobioreactor support bracket 131 of a transom 130 above the photobioreactor 121 and the lower photobioreactor support bracket 133 below the photobioreactor 121 are adapted to connect to the body 135 of the transom 130 and to suspend the photobioreactor 121 therebetween and to suspend the photobioreactor 121 with the air cavity 128 formed by the interior and exterior glass panels 125, 124.

In some embodiment, the transom 130 also includes an anchor 134 that extends into or adjacent to a building support structure 90, such as a floor of the building, and an anchor bolt 136 that is adapted to ensure that the transom 130 remains anchored to the building support structure.

The mullion 140 includes interior glass support brackets 142 and exterior glass support brackets 141 connected to a body 145 thereof. In embodiments, the body 145 is a single body, and in other embodiments, the body 145 is formed of two separate bodies joined together. The interior and exterior glass support brackets 142, 141 are adapted to support the sides interior and exterior glass panels 125, 124. In embodiments, the interior and exterior glass support brackets 142, 141 are adapted to form a seal with the interior and exterior glass panels 125, 124. In the embodiment illustrated, a single mullion 140 is adapted to support a side of a first set of the interior and exterior glass panels 125, 124 and a side of a second set of the interior and exterior glass panels 125, 124. In another embodiment, separate mullions are used to support adjacent sides of two sets of the interior and exterior glass panels 125, 124.

In some embodiments, the mullion 140 is adapted to support the bottom of a second set of the interior and exterior glass panels 125, 124.

As can be seen in FIG. 6, in some embodiments, the mullion 140 and the photobioreactor 121 is adapted to form a gap therebetween. In embodiments, a localized bracket 129 is adapted to connect the photobioreactor 121 to the mullions 140, which provides further support for the photobioreactor 121 from the mullions 140, while maintaining the suspended nature of the photobioreactor 121 between the upper and lower transoms 130.

Referring again to FIG. 5, in embodiments, each of the air outlet line 101, microalgae inlet line 102, air inlet line 103, and microalgae outlet line 104 includes a valve 126 for controlling a flow therethrough. In some embodiments, the valves 126 are control valves that are adapted to be controlled by the controller 200.

In some embodiments, the microalgae curtain wall 120 is a modular component, where the photobioreactor 121, the interior and exterior glass panels 125, 124, the transoms 130 above and below the photobioreactor 121, and the mullions 140 on each side of the photobioreactor 121 are a modular, prefabricated component. In these embodiments, the bodies 135 of adjoining transoms 130 are adapted to connect together to form a single transom 130, and the bodies 145 of adjoining mullions 140 are adapted to connect together to form a single mullion 140.

In embodiments, various designs shapes, materials, and typologies are used for the photobioreactor 121. In the embodiment illustrated in FIGS. 2-6, the photobioreactors 121 include walls formed of at least a semitransparent material, such as a polymer (e.g. bioplastic, Polyethylene terephthalate) or glass (e.g. borosilicate, float), which are adapted to contain the microalgae. In the embodiment illustrated in FIGS. 2-6, the photobioreactor 121 includes an array of divided, diamond or circular shaped, bodies connected by tubes.

In embodiments, the photobioreactor 121 are one of screen types and louver/fin type, which result in the regulation of energy transfer between indoor and outdoor while balancing daylighting, view-out, and solar radiation, all while encouraging microalgae growth, $CO_2$ reduction, and $O_2$ generation.

Figure 7:
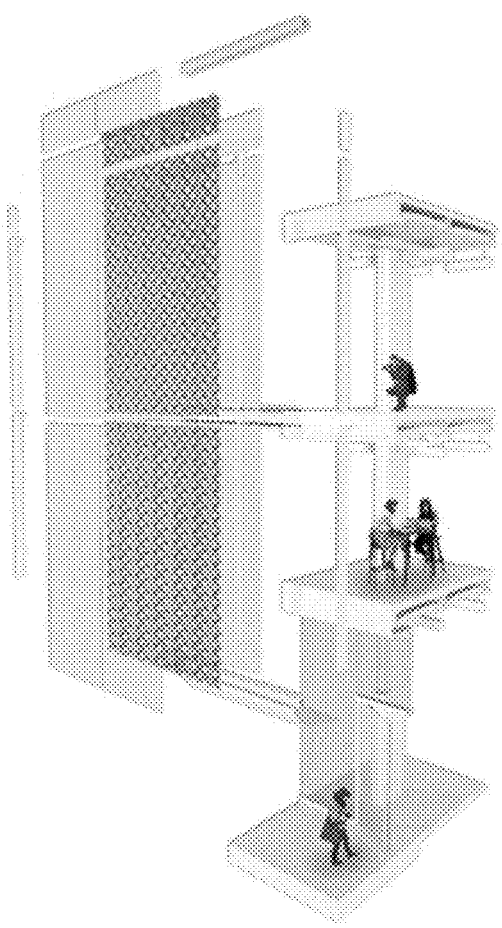
FIG. 7 is a partially exploded schematic illustration of an embodiment of the microalgae curtain wall of FIGS. 1-6.
Figure 8:
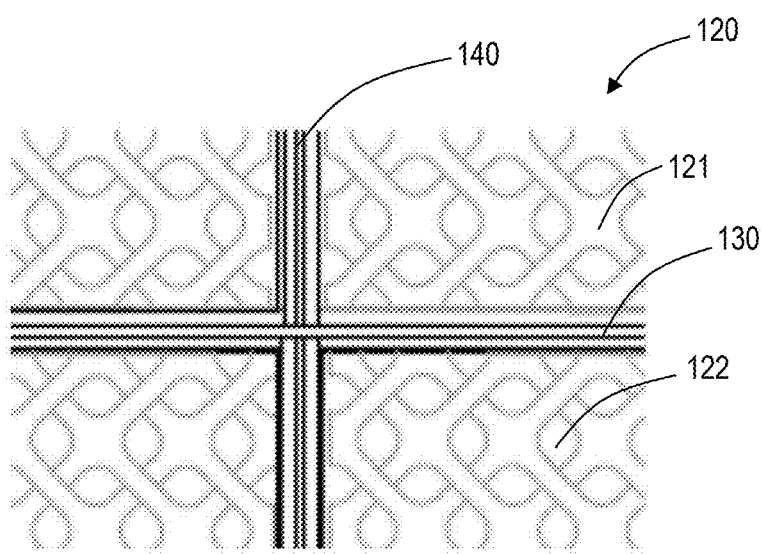
FIG. 8 is a schematic illustration of a partial elevation of the microalgae curtain wall of FIG. 7.
Figure 9:
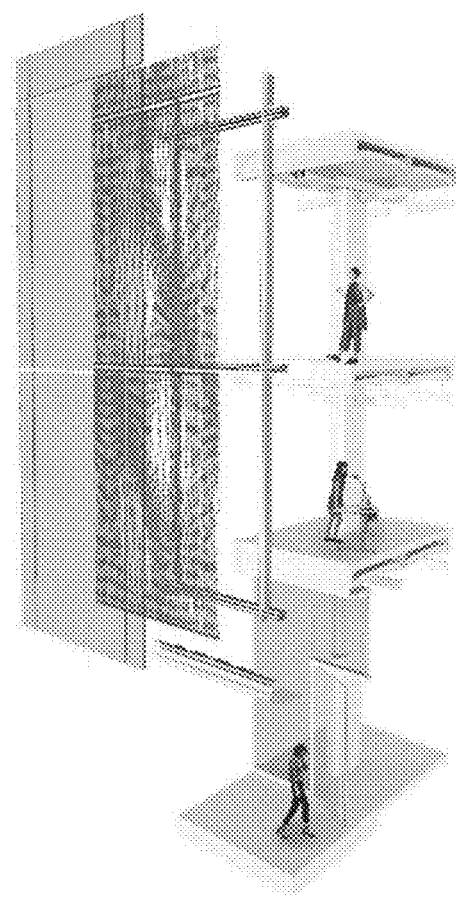
FIG. 9 is a partially exploded schematic illustration of an embodiment of the microalgae curtain wall of FIGS. 1-6.
Figure 10:
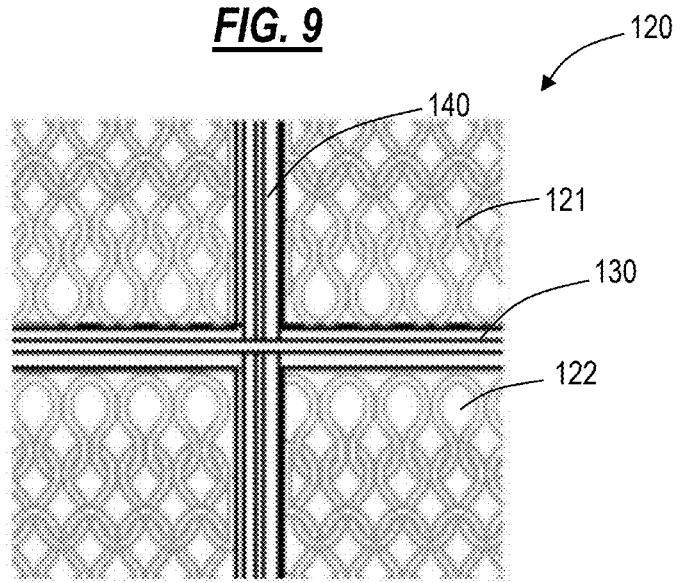
FIG. 10 is a schematic illustration of a partial elevation of the microalgae curtain wall of FIG. 9.

FIG. 7 is a partially exploded schematic illustration of an embodiment of the microalgae curtain wall of FIGS. 1-6. FIG. 8 is a partially exploded schematic illustration of a partial elevation of the microalgae curtain wall of FIG. 7. FIG. 9 is a partially exploded schematic illustration of an embodiment of the microalgae curtain wall of FIGS. 1-6. FIG. 10 is a partially exploded schematic illustration of a partial elevation of the microalgae curtain wall of FIG. 9.

FIGS. 7-10 illustrate varying shapes of the photobioreactors 121 in accordance with various embodiments. Referring to FIGS. 7 and 8, the photobioreactors 121 illustrated are suspended and formed of a continuous and plaited three-dimensional (3D) tubes that alternate between intersecting (fluidly connecting) and overlapping or interlocking (without fluidly connecting) to form a photobioreactor 121 array.

Referring to FIGS. 9 and 10, the photobioreactors 121 illustrated are suspended and are small, woven tubes that overlap with an adjoining weave, such as above and below (as shown) or with each weave to the sides thereof In the embodiment illustrated, each weave is connected to the adjoining weave(s) on the sides thereof, adjacent to the mullions 140. In such a woven topology, a continuous watertight microalgae culture is contained while the density of wefts and warps of the weaves are adjustable to balance the solar exposure for maximum microalgae growth, access to view-out and daylighting potentials while regulating thermal and visual environments.

In embodiments, woven photobioreactors 121 are made of continuous flexible tubing while woven knots provide the geometric stability for the tubing as a photobioreactor. In embodiments, woven photobioreactors 121 are hung within the air cavity 128 as disclosed above. In other embodiments, the woven photobioreactors 121 are cast within resin, which is a glazing layer for the photobioreactors 121. The small diameter of tubing and its flexibility guarantee even solar exposure for microalgae growth.

Figure 11:
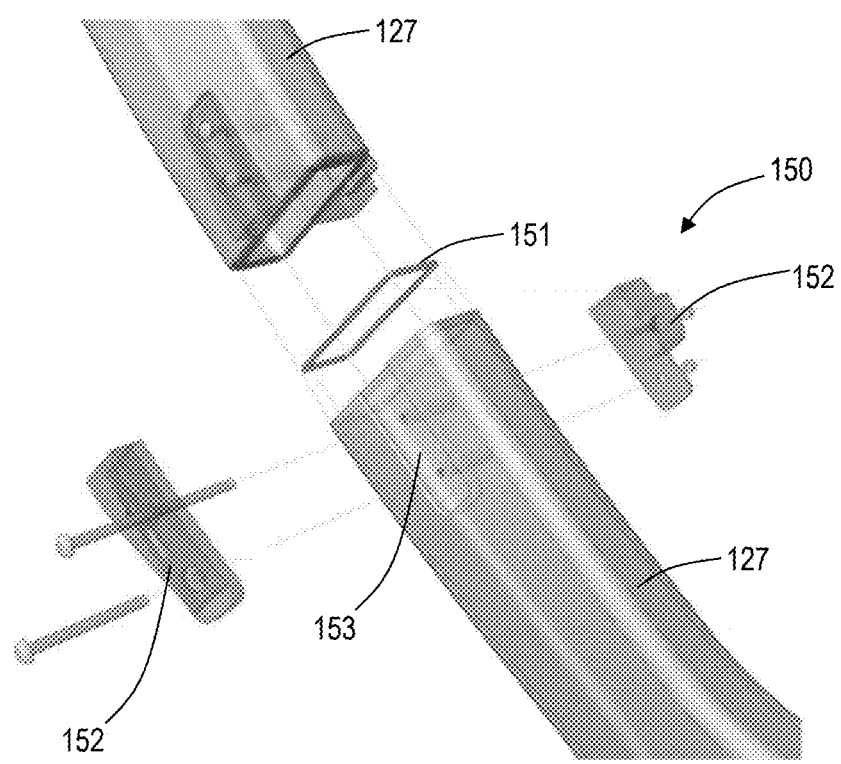
FIG. 11 is an exploded schematic illustration of a joint between adjoining photobioreactor components of the photobioreactor of FIGS. 1-10.

FIG. 11 is an exploded schematic illustration of a joint 150 between adjoining photobioreactor components 127 of the photobioreactor 120 of FIGS. 1-10. In embodiments, the joint 150 includes adjoining photobioreactor components 127, such as tubing, a gasket positioned between the adjoining photobioreactor components 127, a key 153 on each side of the photobioreactor components 127, and one or more brackets 152 adapted to fit within the keys 153 to hold the photobioreactor components 127 together with the gasket 151 held tightly therebetween so as to form a seal. In embodiments, the gasket 151 is formed of silicon. However, other materials are also contemplated.

Figure 14:
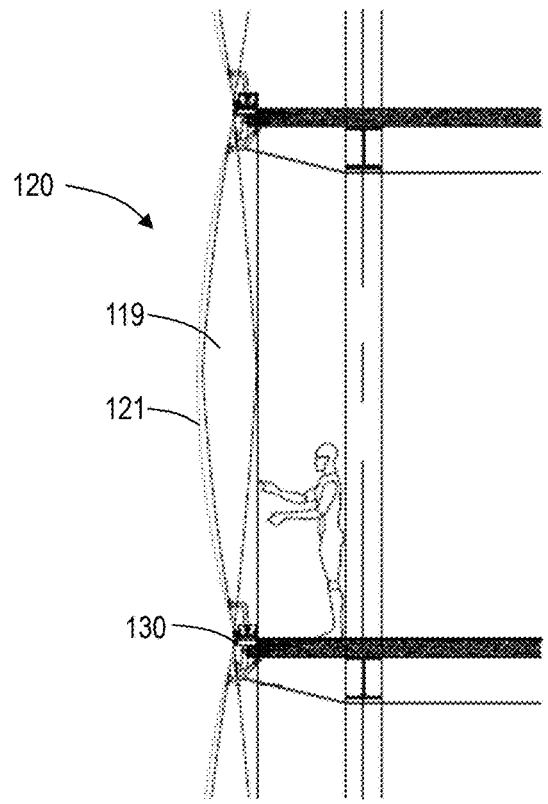
FIG. 14 is a schematic illustration of a cross-section of the microalgae curtain wall of FIG. 13 taken along the line XIV-XIV.
Figure 15:
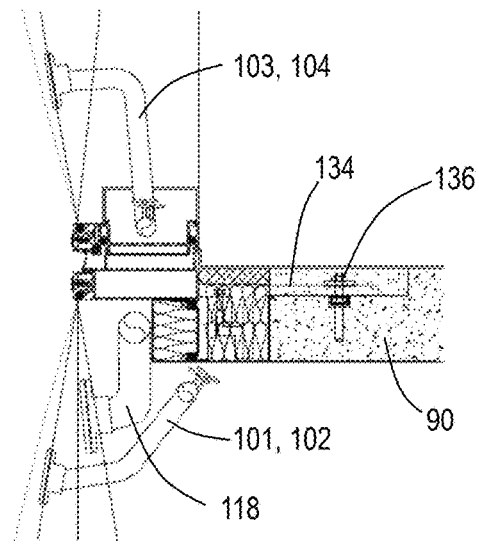
FIG. 15 is a schematic illustration of a partial cross-section of the microalgae curtain wall of FIG. 13 taken along the line XV-XV.
Figure 16:
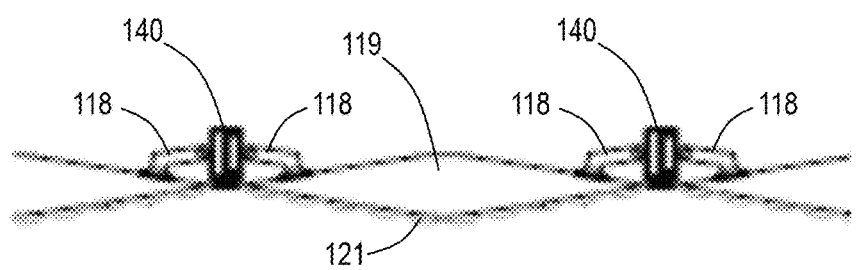
FIG. 16 is a schematic illustration of a partial cross-section of the microalgae curtain wall of FIG. 13 taken along the line XVI-XVI.

FIG. 12 is a partially exploded schematic illustration of an embodiment of the microalgae curtain wall of FIG. 1. FIG. 13 is a schematic illustration of a partial elevation of the microalgae curtain wall of FIG. 12. FIG. 14 is a schematic illustration of a cross-section of the microalgae curtain wall of FIG. 13 taken along the line IX-IX. FIG. 15 is a schematic illustration of a partial cross-section of the microalgae curtain wall of FIG. 13 taken along the line XV-XV. FIG. 16 is a schematic illustration of a partial cross-section of the microalgae curtain wall of FIG. 13 taken along the line XVI-XVI.

Referring to FIGS. 12-16, in embodiments, the microalgae curtain wall 120 includes transoms 130, mullions 140, photobioreactors 121, and inflatable pillows 119. In the embodiment illustrated, the photobioreactors 121 are supported from the top and bottom by transoms 130 and the mullions 140 form a crossing pattern that further supports the photobioreactors 121 by providing support for the inflatable pillows 119.

In embodiments, the inflatable pillows 119 include a body formed of a fluorine based plastic, such as Ethylene tetrafluoroethylene (ETFE) that is adapted to inflate. Air inlet lines 118 are adapted to supply air to the inflatable pillows 119 for inflation thereof. In embodiments, the microalgae system 100 includes a compressor for supplying the air thereto.

The photobioreactors 121 are positioned on an outer surface of the inflatable pillows 119, opposite the building. The photobioreactors 121 and the inflatable pillows 119 form separate, dissociated cavities. In embodiments, the photobioreactors 121 are integrated into the inflatable pillow 119. By integrating the photobioreactors 121 into the inflatable pillows 119, a primary enclosure with good structural, thermal, and solar performance is provided for the building. Further, the integration of photobioreactors 121 within the inflatable pillows 119 provides noise attenuation, such as for noise from rain droplets.

Figure 17:
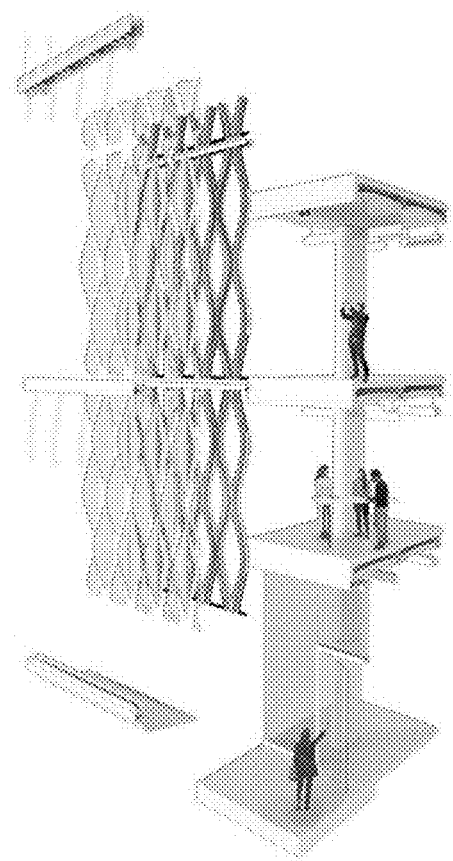
FIG. 17 is a partially exploded schematic illustration of an embodiment of the microalgae curtain wall of FIG. 1.
Figure 18:
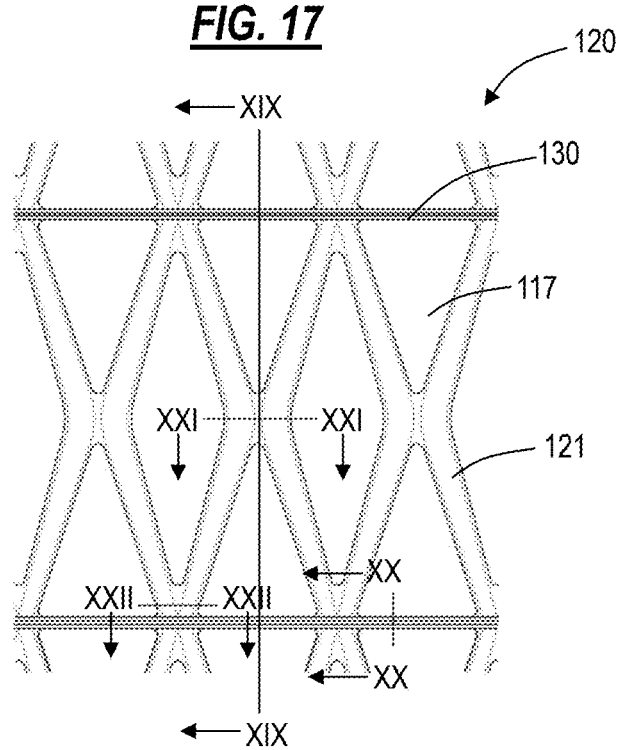
FIG. 18 is a schematic illustration of a partial elevation of the microalgae curtain wall of FIG. 17.
Figure 19:
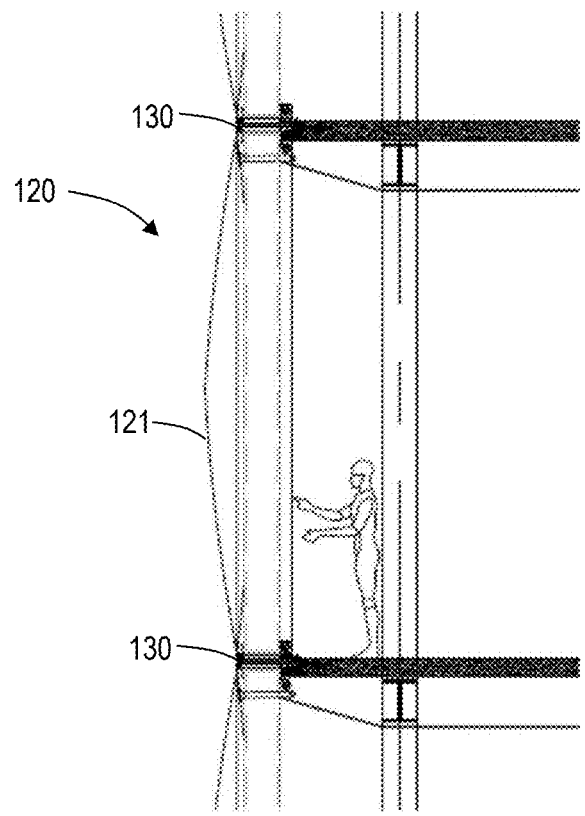
FIG. 19 is a schematic illustration of a cross-section of the microalgae curtain wall of FIG. 18 taken along the line XIX-XIX.
Figure 20:
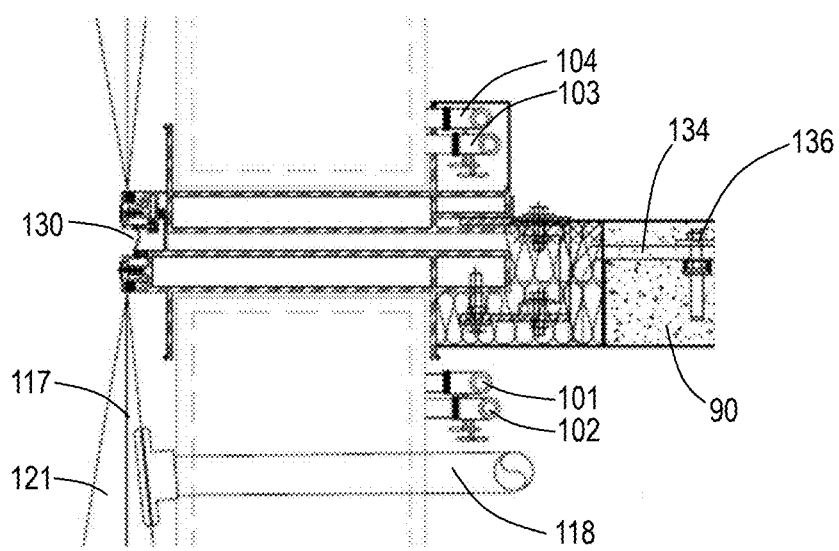
FIG. 20 is a schematic illustration of a partial cross-section of the microalgae curtain wall of FIG. 18 taken along the line XX-XX.
Figure 21:
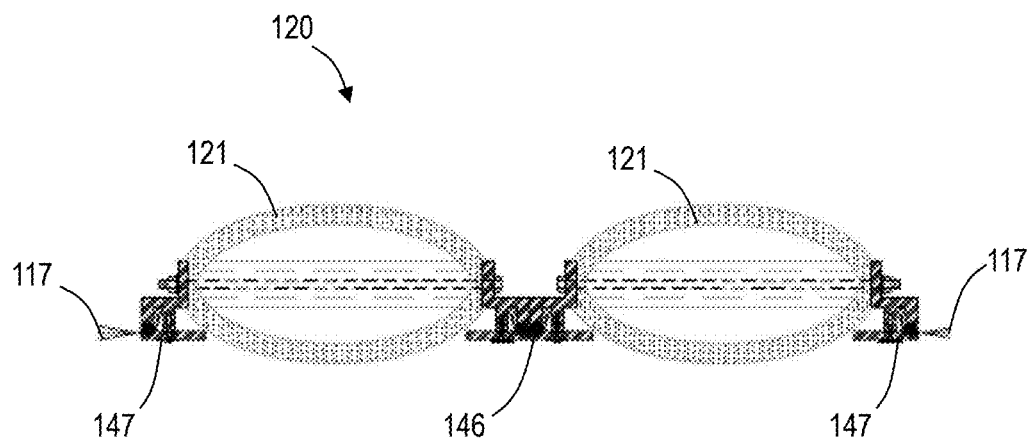
FIG. 21 is a schematic illustration of a partial cross-section of the microalgae curtain wall of FIG. 18 taken along the line XXI-XXI.
Figure 22:
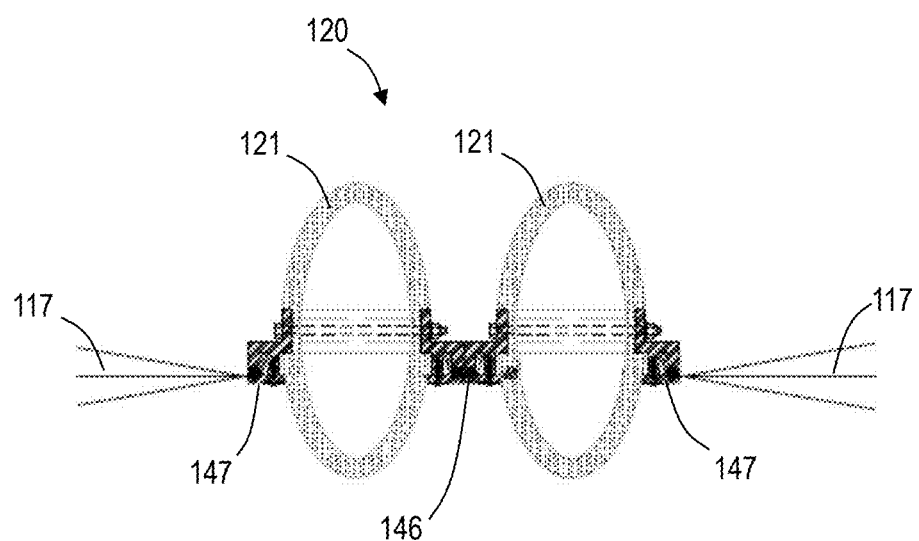
FIG. 22 is a schematic illustration of a partial cross-section of the microalgae curtain wall of FIG. 18 taken along the line XXII-XXII.

FIG. 17 is a partially exploded schematic illustration of an embodiment of the microalgae curtain wall of FIG. 1. FIG. 18 is a schematic illustration of a partial elevation of the microalgae curtain wall of FIG. 17. FIG. 19 is a schematic illustration of a cross-section of the microalgae curtain wall of FIG. 18 taken along the line XIV-XIV. FIG. 20 is a schematic illustration of a partial cross-section of the microalgae curtain wall of FIG. 18 taken along the line XX-XX. FIG. 21 is a schematic illustration of a partial cross-section of the microalgae curtain wall of FIG. 18 taken along the line XXI-XXI. FIG. 22 is a schematic illustration of a partial cross-section of the microalgae curtain wall of FIG. 18 taken along the line XXII-XXII.

Referring to FIGS. 17-22, in embodiments, the microalgae curtain wall 120 includes strands of photobioreactors 121 extending vertically between transoms 130. In embodiments the strands include an arced or wave shape and are connected to adjacent strands at the maximum/minimums of the arcs/waves. In particular, a middle edge adapter 146 is adapted to connect sections of the strands together. In embodiments, the strands of photobioreactors 121 are extrusions and form structural framing of the microalgae curtain-wall 120.

In embodiments, inflatable pillows 117 are adapted to fill the gaps between the strands of photobioreactors 121. In some embodiments, inflatable pillows 117 include a body formed of a fluorine based plastic, such as EFTFE that is adapted to inflate. Air inlet lines 118 are adapted to supply air to the inflatable pillows 117 for inflation thereof. In embodiments, side edge adapters 147 are adapted to connect the inflatable pillows 117 to the strands of photobioreactors 121, such as around a perimeter of the inflatable pillows 117.

As the inflatable pillows 117 are infilled between the photobioreactor extrusions, the inflatable pillows 117 can be adapted to provide view-out, daylight transmittance, waterproofing, airtightness, thermal insulation, and natural ventilation.

Figure 23:
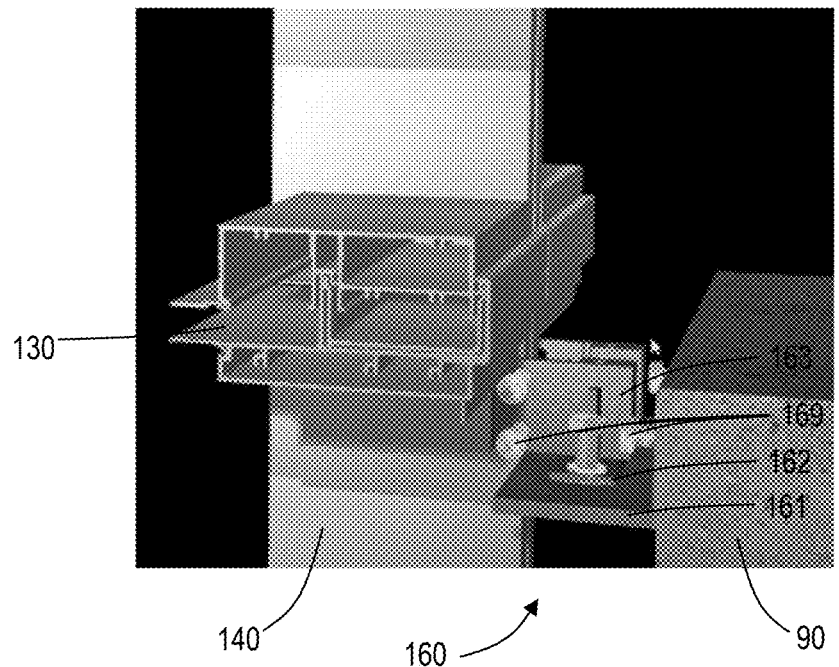
FIG. 23 is a schematic illustration of an embodiment of a mounting bracket assembly for the microalgae curtain wall of FIGS. 1-22.
Figure 24:
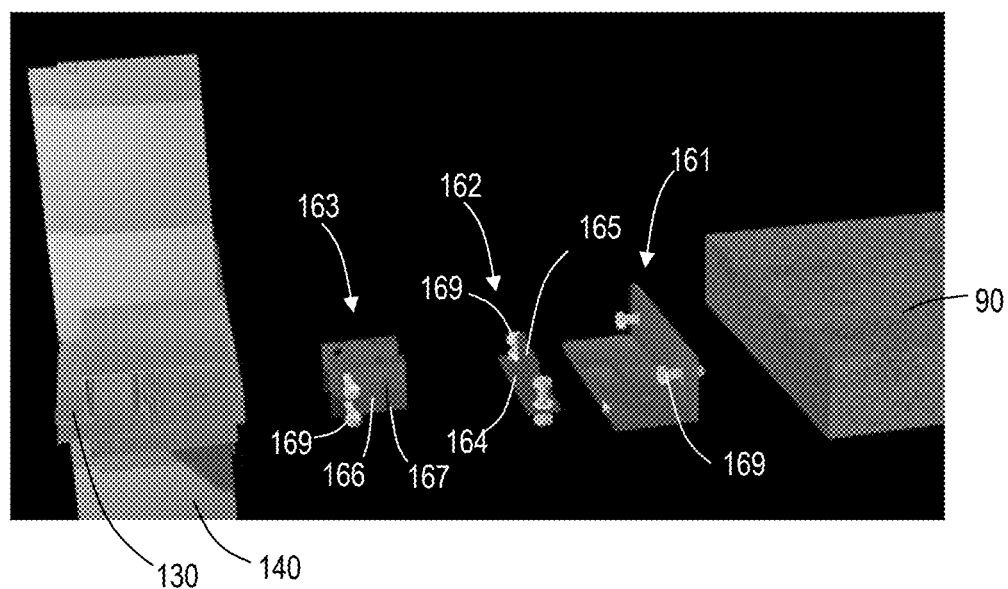
FIG. 24 is an exploded schematic illustration of an embodiment of a mounting bracket assembly for the microalgae curtain wall of FIG. 23.

FIG. 23 is a schematic illustration of an embodiment of a mounting bracket assembly for the microalgae curtain wall of FIGS. 1-22. FIG. 24 is an exploded schematic illustration of an embodiment of a mounting bracket assembly for the microalgae curtain wall of FIG. 23. Referring to FIGS. 23 and 24, in some embodiments, microalgae system 100 includes one or more mounting bracket assemblies 160 adapted to secure the microalgae curtain wall 120 to the building support structure 90.

In embodiments, the mounting bracket assembly 160 is adapted to receive and hold a portion of a mullion 140, such as the portion adjacent to a transom 130. In the embodiment illustrated, the mounting bracket assembly 160 includes an 'L' shaped bracket 161, a slider bracket 162, and a sliding bracket 163. However, other configurations are also contemplated. The 'L' shaped bracket 161 includes a vertical portion adapted to secure to the building support structure 90 by fasteners 169, such as bolts and includes a horizontal portion extending out from the vertical portion.

The slider bracket 162 includes a base 164 and a slider 165. The base is adapted to be joined to the horizontal portion of the 'L' shaped bracket 161 by fasteners 169. The slider extends upward from the base 164 and is adapted to slidably couple with the sliding bracket 163.

The sliding bracket 163 is adapted to receive and be fastened to the mullion 140 by fasteners 169 and is adapted to slidably couple with the slider bracket 162. In the embodiment illustrated, the sliding bracket 163 includes bracket arms 166 that are spaced apart and that receive the mullion 140 therebetween. Each bracket arm 166 includes a slot 167 that is adapted to receive the slider 165. In the embodiment illustrated, the bracket arms 166 are adapted to be transverse, such as orthogonal, to each of the base 164, the slider 165, and the vertical and horizontal portions of the 'L' shaped bracket 161.

Figure 25:
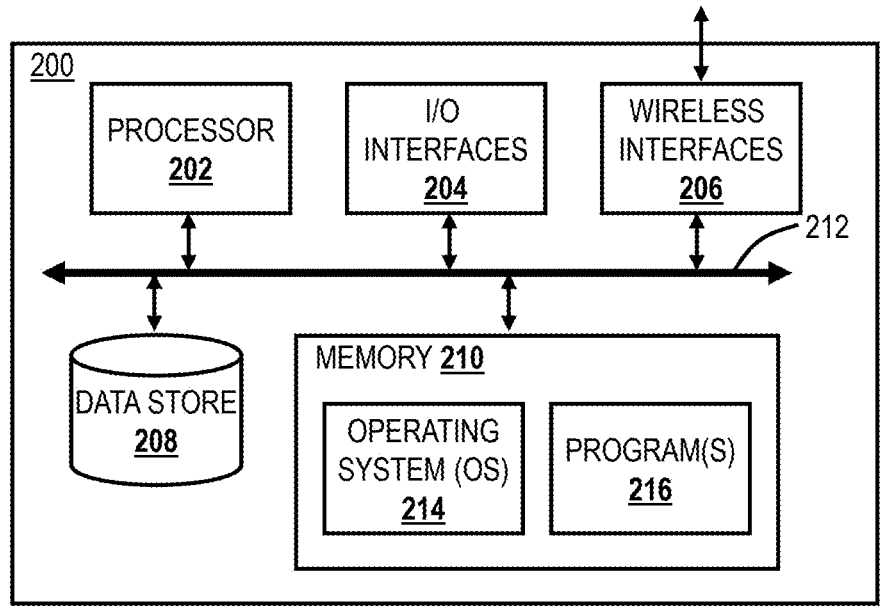
FIG. 25 is a block diagram of the controller of FIG. 1.

FIG. 25 is a block diagram of the controller 200 of FIG. 1. The controller 200 can be a digital device that, in terms of hardware architecture, generally includes a processor 202, input/output (I/O) interfaces 204, wireless interfaces 206, a data store 208, and memory 210. It should be appreciated by those of ordinary skill in the art that FIG. 25 depicts the controller 200 in an oversimplified manner, and a practical embodiment may include additional components and suitably configured processing logic to support known or conventional operating features that are not described in detail herein. The components (202, 204, 206, 208, and 202) are communicatively coupled via a local interface 212. The local interface 212 can be, for example, but not limited to, one or more buses or other wired or wireless connections, as is known in the art. The local interface 212 can have additional elements, which are omitted for simplicity, such as controllers, buffers (caches), drivers, repeaters, and receivers, among many others, to enable communications. Further, the local interface 212 may include address, control, and/or data connections to enable appropriate communications among the aforementioned components.

The processor 202 is a hardware device for executing software instructions. The processor 202 can be any custom made or commercially available processor, a central processing unit (CPU), an auxiliary processor among several processors associated with the controller 200, a semiconductor-based microprocessor (in the form of a microchip or chip set), or generally any device for executing software instructions. When the controller 200 is in operation, the processor 202 is configured to execute software stored within the memory 210, to communicate data to and from the memory 210, and to generally control operations of the controller 200 pursuant to the software instructions. The I/O interfaces 204 can be used to receive user input from and/or for providing system output. User input can be provided via, for example, a keypad, a touch screen, a scroll ball, a scroll bar, buttons, barcode scanner, and the like. System output can be provided via a display device such as a liquid crystal display (LCD), touch screen, and the like. The I/O interfaces 204 can also include, for example, a serial port, a parallel port, a small computer system interface (SCSI), an infrared (IR) interface, a radio frequency (RF) interface, a universal serial bus (USB) interface, and the like. The I/O interfaces 204 can include a graphical user interface (GUI) that enables a user to interact with the controller 200.

The wireless interfaces 206 enable wireless communication to an external access device or network. Any number of suitable wireless data communication protocols, techniques, or methodologies can be supported by the wireless interfaces 206, including, without limitation: RF; IrDA (infrared); Bluetooth; ZigBee (and other variants of the IEEE 802.15 protocol); IEEE 802.11 (any variation); IEEE 802.16 (WiMAX or any other variation); Direct Sequence Spread Spectrum; Frequency Hopping Spread Spectrum; Long Term Evolution (LTE); cellular/wireless/cordless telecommunication protocols (e.g. 3G/4G, etc.); wireless home network communication protocols; paging network protocols; magnetic induction; satellite data communication protocols; wireless hospital or health care facility network protocols such as those operating in the WMTS bands; GPRS; proprietary wireless data communication protocols such as variants of Wireless USB; and any other protocols for wireless communication. The wireless interfaces 206 can be used to communicate with external networks for receiving command and control instructions as well as to relay data.

The data store 208 may be used to store data. The data store 208 may include any of volatile memory elements (e.g., random access memory (RAM, such as DRAM, SRAM, SDRAM, and the like)), nonvolatile memory elements (e.g., ROM, hard drive, tape, CDROM, and the like), and combinations thereof. Moreover, the data store 208 may incorporate electronic, magnetic, optical, and/or other types of storage media. The memory 110 may include any of volatile memory elements (e.g., random access memory (RAM, such as DRAM, SRAM, SDRAM, etc.)), nonvolatile memory elements (e.g., ROM, hard drive, etc.), and combinations thereof. Moreover, the memory 210 may incorporate electronic, magnetic, optical, and/or other types of storage media. Note that the memory 210 may have a distributed architecture, where various components are situated remotely from one another but can be accessed by the processor 202. The software in memory 210 can include one or more software programs, each of which includes an ordered listing of executable instructions for implementing logical functions. In the example of FIG. 25, the software in the memory 210 includes a suitable operating system (O/S) 214 and programs 216. The operating system 214 essentially controls the execution of other computer programs and provides scheduling, input-output control, file and data management, memory management, and communication control and related services. The programs 216 may include various applications, add-ons, etc. configured to provide end-user functionality with the controller 200, including performing various aspects of the systems and methods described herein.

It will be appreciated that some embodiments described herein may include or utilize one or more generic or specialized processors ("one or more processors") such as microprocessors; Central Processing Units (CPUs); Digital Signal Processors (DSPs): customized processors such as Network Processors (NPs) or Network Processing Units (NPUs), Graphics Processing Units (GPUs), or the like; Field-Programmable Gate Arrays (FPGAs); and the like along with unique stored program instructions (including both software and firmware) for control thereof to implement, in conjunction with certain non-processor circuits, some, most, or all of the functions of the methods and/or systems described herein. Alternatively, some or all functions may be implemented by a state machine that has no stored program instructions, or in one or more Application-Specific Integrated Circuits (ASICs), in which each function or some combinations of certain of the functions are implemented as custom logic or circuitry. Of course, a combination of the aforementioned approaches may be used. For some of the embodiments described herein, a corresponding device in hardware and optionally with software, firmware, and a combination thereof can be referred to as "circuitry configured to," "logic configured to," etc. perform a set of operations, steps, methods, processes, algorithms, functions, techniques, etc. on digital and/or analog signals as described herein for the various embodiments.

Moreover, some embodiments may include a non-transitory computer-readable medium having instructions stored thereon for programming a computer, server, appliance, device, processor, circuit, etc. to perform functions as described and claimed herein. Examples of such non-transitory computer-readable medium include, but are not limited to, a hard disk, an optical storage device, a magnetic storage device, a Read-Only Memory (ROM), a Programmable ROM (PROM), an Erasable PROM (EPROM), an Electrically EPROM (EEPROM), Flash memory, and the like. When stored in the non-transitory computer-readable medium, software can include instructions executable by a processor or device (e.g., any type of programmable circuitry or logic) that, in response to such execution, cause a processor or the device to perform a set of operations, steps, methods, processes, algorithms, functions, techniques, etc. as described herein for the various embodiments.

Figure 26:
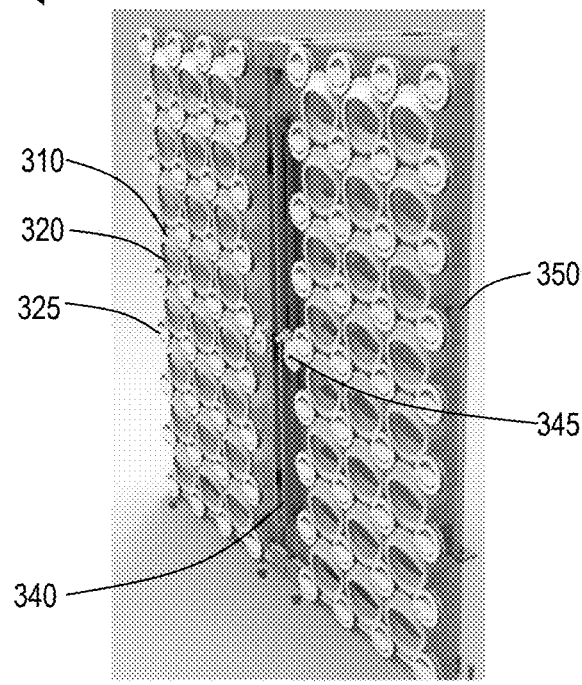
FIG. 26 is a schematic illustration of a micro-oculi building enclosure system.
Figure 27:
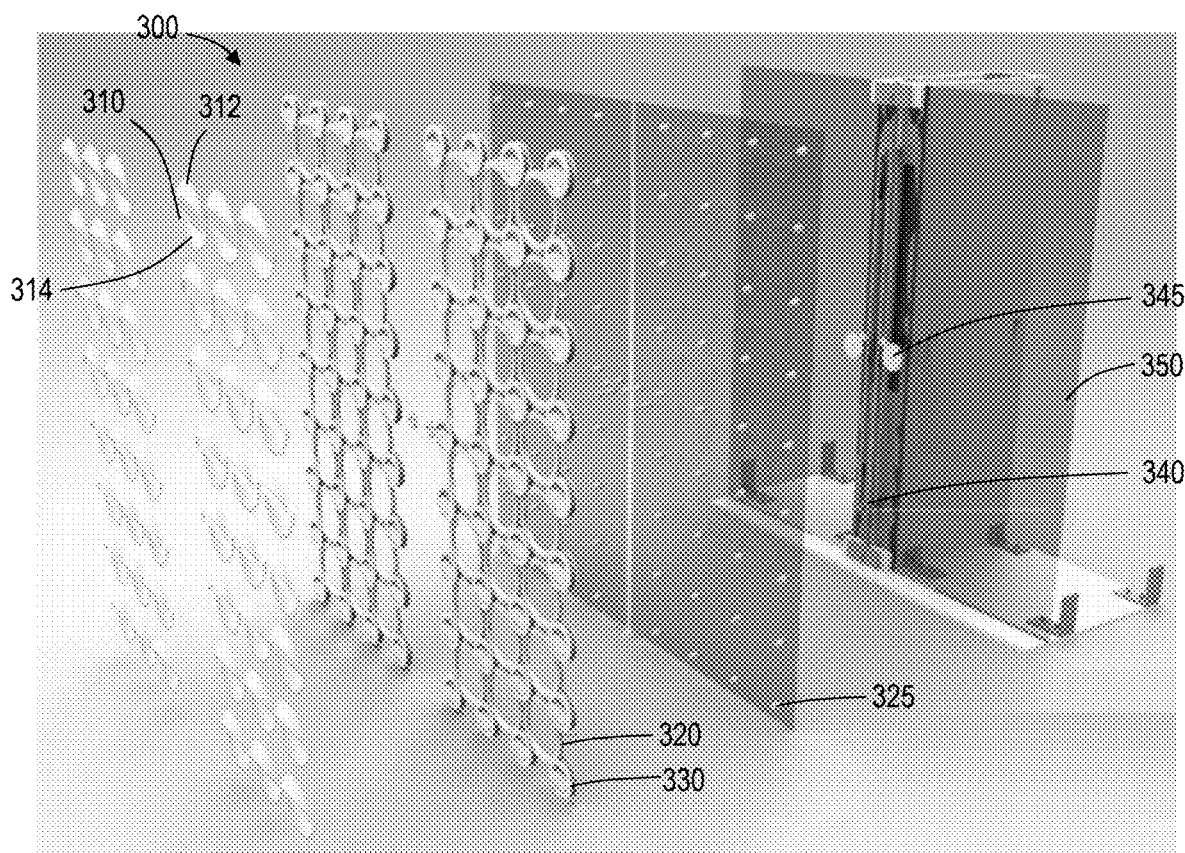
FIG. 27 is an exploded schematic illustration of the micro-oculi building enclosure system of FIG. 26.
Figure 28:
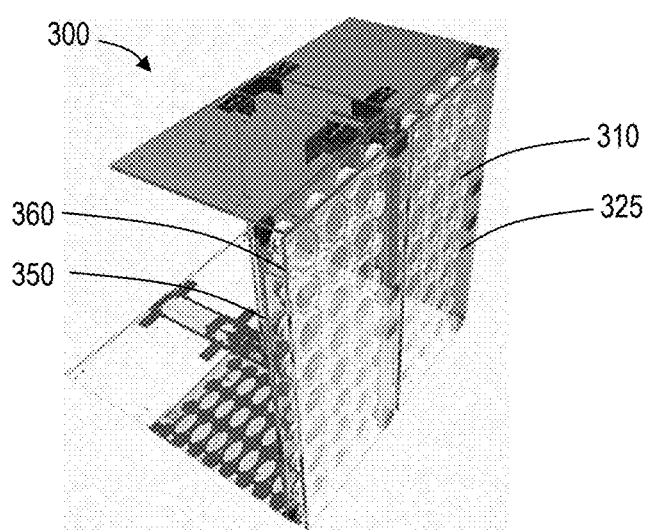
FIG. 28 is a schematic illustration of an embodiment of the micro-oculi building enclosure system of FIG. 26.
Figure 29:
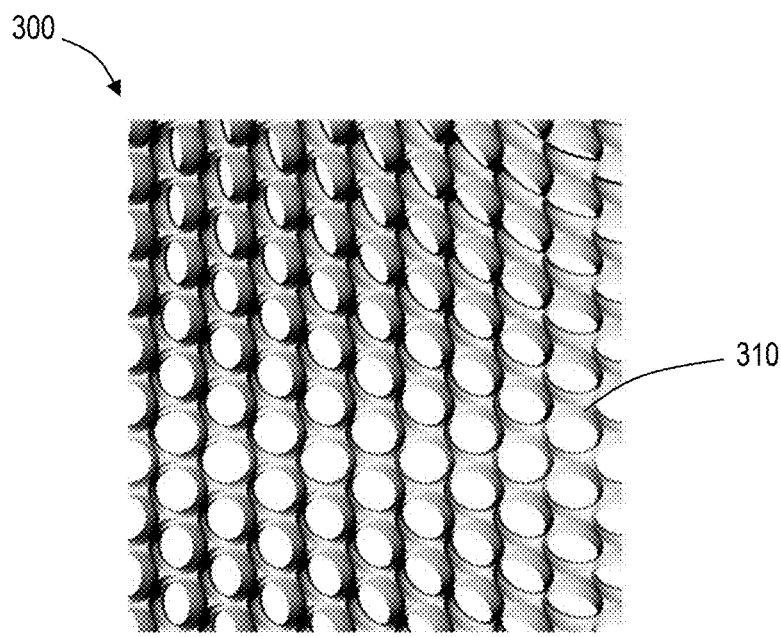
FIG. 29 is a schematic illustration of an alternate embodiment of micro-oculi building enclosure system of FIG. 26.

FIG. 26 is a schematic illustration of a micro-oculi building enclosure system 300. FIG. 27 is an exploded schematic illustration of the micro-oculi building enclosure system 300 of FIG. 26. FIG. 28 is a schematic illustration of an embodiment of the micro-oculi building enclosure system 300 of FIG. 26. FIG. 29 is a schematic illustration of an alternate embodiment of micro-oculi building enclosure system 300 of FIG. 26.

Referring to FIGS. 26-29, the micro-oculi building enclosure system 300 includes micro-oculus shaders 310. The micro-oculus shaders 310 are one of statically oriented, such as in the static system illustrated in FIG. 29, and adapted to dynamically rotate, such as in the dynamic system illustrated in FIGS. 26-28. The geometry and movements of kinetic micro-oculi device are optimized for solar gain, daylighting, and views, and in particular for solar power production. In embodiments, micro-oculi building enclosure system 300 is a prefabricated unit that serves as a primary building enclosure.

In embodiments, the micro-oculus shaders 310 are mounted on an interior glass pane 350. And in some embodiments, such as the embodiment illustrated in FIG. 28, the micro-oculus shaders 310 are mounted between an interior glass pane 350 and an exterior glass pane 360. In embodiments, the interior glass pane 350 and the exterior glass pane 360 form an insulated glass unit, which provides insulation for the building. Both the kinetic and static systems provide adequate thermal and structural performance, good daylight transmission, shading efficacy, longevity, as well as air tightness and water tightness in accordance with industry standards.

In embodiments, the micro-oculus shaders 310 include photovoltaic elements, such as organic photovoltaic elements, for solar energy production. Each of the micro-oculus shaders 310 includes an ocular shape with an upper shading portion 312 and a lower shading portion 314. The upper shading portion 312 protrudes outward from a circular base of the micro-oculus shader 310 in the axial direction relative to the base and at least partially toward the axis of the base. The lower shading portion 314 protrudes outward from the circular base of the micro-oculus shader 310 in the axial direction relative to the axis of the base and at least partially away from the axis of the base. In embodiments, the upper shading portion 312 and the lower shading portion 314 generally include a hollow cylindrical wedge shape with an axis that is at a different angle than that of the base.

The upper shading portion 312 is adapted to partially block light passing through the micro-oculus shader 310, while the lower shading portion 314 is adapted to reflect light passing adjacent to the micro-oculus shader 310.

In embodiments, the dynamic system includes a gear chain 340, at least one driving gear 345, oculus rotation gears 320, and interstitial rotation gears 330. The gear chain 340 is adapted to rotate the micro-oculus shaders 310. In particular, the gear chain 340 is adapted to rotate the driving gear(s) 345. Each driving gear 345 is adapted to drive rotation of one of an oculus rotation gear 320 and an interstitial rotation gear 330. In the embodiment illustrated, each driving gear 345 is in a geared relationship with an interstitial gear anchor 325. Each oculus rotation gear 320 is adapted to rotate a micro-oculus shader 310. While the oculus rotation gears 320 are shown as separate devices in the embodiment shown, in embodiments, the oculus rotation gear 320 and the corresponding micro-oculus shader 310 are unitary structure that is a single structurally formed entity.

The interstitial rotation gears 330 are positioned between adjacent oculus rotation gears 320 and are adapted to transmit rotation between the adjacent oculus rotation gears 320. In the embodiment illustrated, the interstitial rotation gears 330 are in a geared relationship with four oculus rotation gears 320 when positioned in an interior of the dynamic system, are in a geared relationship with two oculus rotation gears 320 when positioned along a side of the dynamic system, and in a geared relationship with one oculus rotation gear 320 when positioned at a corner of the dynamic system.

In the embodiment illustrated, each interstitial rotation gear 330 is rotationally mounted to one of the glass panes 350, 360 via a mounting pin 330, and the interstitial rotation gears 330 are adapted to hold the micro-oculus shaders 310 in place via the oculus rotation gears 320. With the rotation of the micro-oculus shaders 310, an amount of light passing therethrough and into the building is controllable. Further, with integrated photovoltaic elements, the micro-oculus shaders 310 can be rotated to the optimum angle for energy production.

Figure 30:
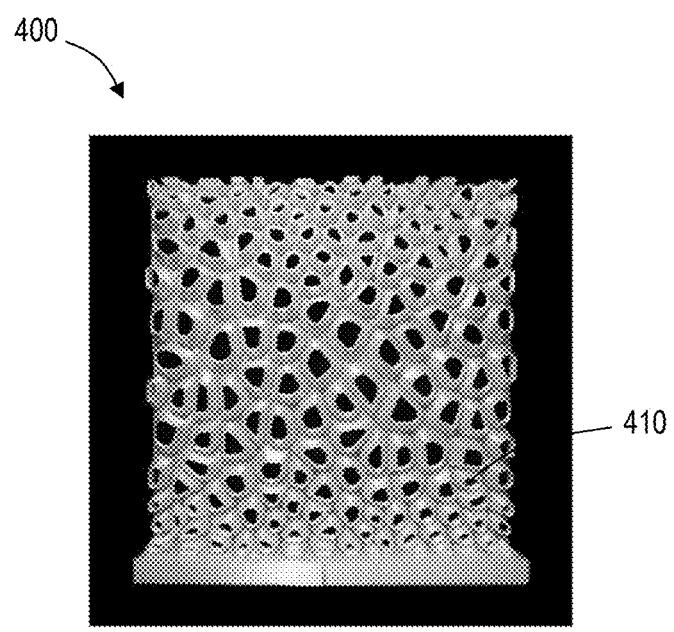
FIG. 30 is a schematic illustration of a photocatalytic enclosure system.
Figure 31:
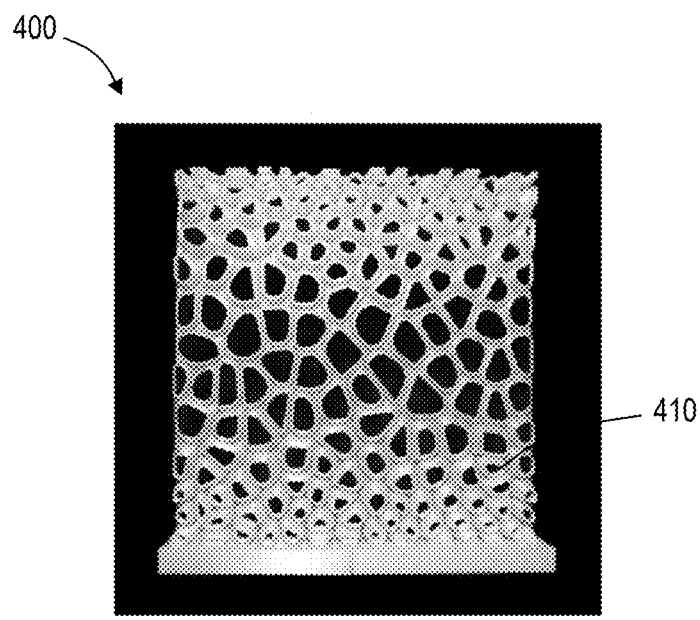
FIG. 31 is a schematic illustration of an alternate layout of the photocatalytic enclosure system of FIG. 30
Figure 32:
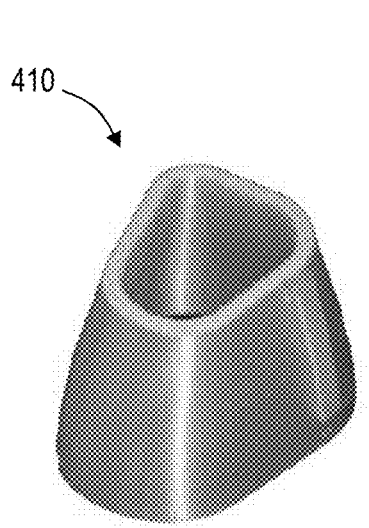
FIG. 32 is schematic illustration of an open cell of the photocatalytic enclosure system of FIG. 30.
Figure 33:
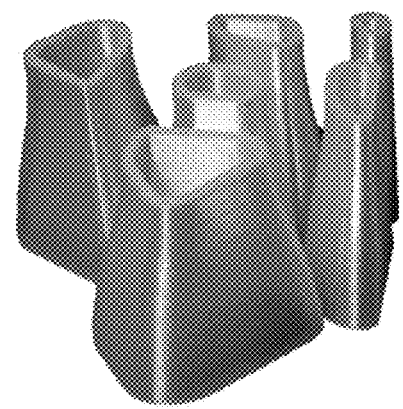
FIG. 33 is a schematic illustration of alternate shapes for the open cell of FIG. 32.

FIG. 30 is a schematic illustration of a photocatalytic enclosure system 400. FIG. 31 is a schematic illustration of an alternate layout of the photocatalytic enclosure system 400 of FIG. 30. FIG. 32 is schematic illustration of an open cell 410 of the photocatalytic enclosure system 400 of FIG. 30. FIG. 33 is a schematic illustration of alternate shapes for the open cell 410 of FIG. 32.

Referring to FIGS. 30-33, the photocatalytic enclosure system 400 includes an array of open cells 410. In embodiments, the array of open cells is 410 formed as a unitary structure that is a single structurally formed entity. In embodiments, the photocatalytic enclosure system 400 is a prefabricated unit with cost-effective constructability and long-term durability.

In embodiments, the open cells 410 are coated with Titanium Dioxide ($TiO_2$). Due to the $TiO_2$, the photocatalytic enclosure system 400 operates as a smog eating facade, as the $TiO_2$ acts as a catalyst activated by solar UV to remove common urban smog such as NO, $NO_2$, SO, and VOCs.

The open cells 410 are 3D open cells that are optimized to balance daylighting, solar radiation, and air purification. This acts as a daylight reflection and/or shading device. In embodiments, the photocatalytic enclosure system 400 is installed at one of outside of a window and inside of a window. In embodiments, the photocatalytic enclosure system 400 is encapsulated between a double skin facade where external air flows through and is purified. The geometry and scale of the photocatalytic 3D cells are optimized based on facade orientations, site locations, and wind (air flow) characteristics. In embodiments, the material of the open cells 410 is one of be opaque, translucent, and transparent depending on the priority of performance requirements (e.g. air purification, daylighting penetration, solar shading, and view-out). Materials range from lightweight fiber concrete, fiber plastics, clear polymers, ceramics, terracotta, and metal.

The photocatalytic enclosure system 400 also serves as a light reflection and shading device that can maximize daylighting while minimizing energy consumption from heating, cooling, and artificial light loads. This energy efficiency will offset $CO_2$ emission by burning fossil fuels.

Although the present disclosure has been illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present disclosure, are contemplated thereby, and are intended to be covered by the following claims.

What is claimed is:

1. A microalgae curtain wall, comprising:
   photobioreactors adapted to receive sunlight and carbon dioxide to grow microalgae received therein;
   an interior glass panel;
   an exterior glass panel offset from the interior glass panel forming a gap therebetween;
   transoms holding the interior glass panel and the exterior glass panel therebetween, the transoms suspending the photobioreactors in the gap between the interior glass panel and the exterior glass panel, wherein the transoms include at least one upper photobioreactor support bracket and at least one lower photobioreactor support bracket with vertically slotted holes that hold and suspend the photobioreactors therebetween;
   mullions holding the interior glass panel and the exterior glass panel therebetween and positioned at sides of the photobioreactors; and
   mounting bracket assemblies configured to secure the microalgae curtain wall to a building support structure, each mounting bracket assembly holding a portion of an associated mullion adjacent to an associated transom, each mounting bracket assembly comprising an 'L' shaped bracket, a slider bracket, and a sliding bracket, wherein the 'L' shaped bracket of each mounting bracket assembly includes a vertical portion configured to be secured to the building support structure by one or more fasteners and a horizontal portion extending out from the vertical portion,
   wherein each of the transoms and the mullions include glass support brackets for the interior glass panel and the exterior glass panel, forming a seal therewith, and wherein the transoms, the mullions, the interior glass panel, and the exterior glass panel form an insulated glass structure, and
   wherein the microalgae curtain wall is an integrated system configured as a window for a building, and the photobioreactors are arranged in an array forming open vision areas interspersed within the array that are adapted to allow a view out and daylight penetration into the building.

2. The microalgae curtain wall of claim 1, wherein the microalgae curtain wall, including the transoms, the mullions, the interior glass panel, the exterior glass panel, and the photobioreactors, forms a modular, prefabricated component.

3. The microalgae curtain wall of claim 1, wherein the photobioreactors include multiple photobioreactor components joined together by one or more brackets with a gasket therebetween.

4. The microalgae curtain wall of claim 3, wherein each of the photobioreactor components includes a key on opposing sides with the one or more brackets received therein.

5. The microalgae curtain wall of claim 1, wherein the array of photobioreactors is arranged with at least one of a partially overlapping or interlocking pattern.

6. The microalgae curtain wall of claim 1, further comprising:
   inflatable pillows, each inflatable pillow configured to support a photobioreactor relative to at least a portion of the mullions.

7. The microalgae curtain wall of claim 1, wherein the slider bracket includes a base and a slider portion, the base joined to the horizontal portion of the 'L' shaped bracket via one or more fasteners such that the slider portion of the first slider extends upward from the base to slidably couple with the sliding bracket.

8. The microalgae curtain wall of claim 7, wherein the sliding bracket is fastened to the associated mullion such that the associated mullion is slidably coupled with slider bracket.

9. The microalgae curtain wall of claim 8, wherein the sliding bracket includes bracket arms that are spaced apart and receive the associated mullion therebetween, and wherein each bracket arm defines a slot that receives the slider portion of the slider bracket.

10. The microalgae curtain wall of claim 9, wherein each bracket arm of the sliding bracket of each mounting bracket assembly is oriented transverse to both the base and the slider portion of the of the associated slider bracket and is oriented transverse to both the vertical portion and the horizontal portion of the associated 'L' shaped bracket.

11. The microalgae curtain wall of claim 7, wherein the sliding bracket includes bracket arms that are spaced apart and receive the associated mullion therebetween, and wherein each bracket arm of the sliding bracket of each mounting bracket assembly is oriented transverse to both the base and the slider portion of the of the associated slider bracket and is oriented transverse to both the vertical portion and the horizontal portion of the associated 'L' shaped bracket.

12. A microalgae system, comprising:
a microalgae storage tank adapted to store microalgae cultures; and
a microalgae curtain wall including
photobioreactors adapted to receive the microalgae cultures from the microalgae storage tank and to grow microalgae,
an interior glass panel,
an exterior glass panel offset from the interior glass panel forming a gap therebetween,
transoms holding the interior glass panel and the exterior glass panel therebetween, the transoms suspending the photobioreactors in the gap between the interior glass panel and the exterior glass panel, wherein the transoms include at least one upper photobioreactor support bracket and at least one lower photobioreactor support bracket with vertically slotted holes that hold and suspend the photobioreactors therebetween;
mullions holding the interior glass panel and the exterior glass panel therebetween and positioned at sides of the photobioreactors; and
mounting bracket assemblies configured to secure the microalgae curtain wall to a building support structure, each mounting bracket assembly holding a portion of an associated mullion adjacent to an associated transom, each mounting bracket assembly comprising an 'L' shaped bracket, a first bracket, and a sliding bracket, wherein the 'L' shaped bracket of each mounting bracket assembly includes a vertical portion configured to be secured to the building support structure by one or more fasteners and a horizontal portion extending out from the vertical portion,
wherein each of the transoms and the mullions include glass support brackets for the interior glass panel and the exterior glass panel, forming a seal therewith, and wherein the transoms, the mullions, the interior glass panel, and the exterior glass panel form an insulated glass structure, and
wherein the microalgae curtain wall is an integrated system configured as a window for a building, and the photobioreactors are arranged in an array forming open vision areas interspersed within the array that are adapted to allow a view out and daylight penetration into the building.

13. The microalgae system of claim 12, wherein the photobioreactors include multiple photobioreactor components joined together by one or more brackets with a gasket therebetween.

14. The microalgae system of claim 12, further comprising an oxygen outlet line adapted to supply the oxygen produced by the microalgae to a heating, ventilation, and air conditioning system of the building.

15. The microalgae system of claim 12, further comprising onsite energy production adapted to receive the microalgae from the microalgae curtain wall and convert the microalgae into energy.

16. The microalgae system of claim 12, further comprising a dewatering plant adapted to separate the microalgae from the microalgae curtain wall and water therein.

17. The microalgae system of claim 12, wherein the microalgae curtain wall, including the transoms, the mullions, the interior glass panel, the exterior glass panel, and the photobioreactors, forms a modular component, and wherein the microalgae system includes a plurality of the modular component.

* * * * *